United States Patent
Iio et al.

(10) Patent No.: US 8,029,525 B2
(45) Date of Patent: Oct. 4, 2011

(54) PUNCTURE INSTRUMENT, PUNCTURE NEEDLE CARTRIDGE, PUNCTURE INSTRUMENT SET, AND PUNCTURE NEEDLE DISPOSAL INSTRUMENT

(75) Inventors: Toshiaki Iio, Saijo (JP); Yoshinori Amano, Saijo (JP); Seiji Kikuchi, Matsuyama (JP)

(73) Assignee: Panasonic Corporation, Osaka (JP)

( * ) Notice: Subject to any disclaimer, the term of this patent is extended or adjusted under 35 U.S.C. 154(b) by 394 days.

(21) Appl. No.: 10/566,434

(22) PCT Filed: Jul. 30, 2004

(86) PCT No.: PCT/JP2004/011301
§ 371 (c)(1),
(2), (4) Date: Jan. 31, 2006

(87) PCT Pub. No.: WO2005/011496
PCT Pub. Date: Feb. 10, 2005

(65) Prior Publication Data
US 2006/0229652 A1 Oct. 12, 2006

(30) Foreign Application Priority Data

Jul. 31, 2003 (JP) ................................. 2003-283328
Sep. 9, 2003 (JP) ................................. 2003-316865

(51) Int. Cl.
*A61B 17/32* (2006.01)
(52) U.S. Cl. ........................... 606/182; 600/583; 401/32
(58) Field of Classification Search .................. 600/583; 606/182; 604/192; 221/75
See application file for complete search history.

(56) References Cited

U.S. PATENT DOCUMENTS

| 2,701,077 | A | * | 2/1955 | Palmer ............................. 221/75 |
| 3,030,959 | A | * | 4/1962 | Grunert ........................... 606/182 |
| 3,708,235 | A | * | 1/1973 | Kolomeir .......................... 401/57 |
| 3,898,009 | A | * | 8/1975 | Christensen ..................... 401/57 |
| 4,794,926 | A |   | 1/1989 | Munsch et al. |
| 4,801,013 | A |   | 1/1989 | Bruno ............................ 206/366 |
| 4,995,402 | A | * | 2/1991 | Smith et al. .................... 600/584 |
| 5,957,601 | A | * | 9/1999 | Weiss ............................. 401/18 |
| 6,045,567 | A |   | 4/2000 | Taylor et al. |
| 6,093,156 | A | * | 7/2000 | Cunningham et al. ........ 600/573 |
| 6,616,616 | B2 |  | 9/2003 | Fritz et al. |
| D491,604 | S | * | 6/2004 | Yeh ................................ D19/36 |
| 2003/0050655 | A1 | * | 3/2003 | Roe ................................ 606/182 |

(Continued)

FOREIGN PATENT DOCUMENTS

CA 2201530 9/1997

(Continued)

*Primary Examiner* — Max Hindenburg
*Assistant Examiner* — Renee Danega
(74) *Attorney, Agent, or Firm* — Steptoe & Johnson LLP

(57) ABSTRACT

An arrangement comprises a puncturing instrument including a cylindrical box, a plurality of puncturing needles held in an axially serially connected state, a locking member for locking the puncturing needle cartridge at an axial predetermined position, and an elastic urging member urging the puncturing needle cartridge in one direction, and a puncturing needle replacing jig which allows the setting of a puncturing position for the puncturing needle cartridge and the discarding of used puncturing needles, in order to enter into a subsequent puncturing action after the puncturing of the puncturing needle. Thus, it is an object to provide, in an instrument for puncturing the surface of a living body, a highly safe puncturing instrument set having a plurality of puncturing needles, capable of continuous puncturing action by a simple operation.

32 Claims, 19 Drawing Sheets

U.S. PATENT DOCUMENTS

2003/0114609 A1 * 6/2003 Samson .................. 526/86

FOREIGN PATENT DOCUMENTS

| DE | 1 079 275 |   | 4/1960 |
|----|-----------|---|--------|
| EP | 0 861 670 |   | 2/1998 |
| FR | 2797579   | * | 8/1999 |
| FR | 2797579   |   | 2/2001 |
| JP | 06-23505  |   | 3/1994 |
| JP | 3030234   |   | 10/1996 |
| JP | 2000166902 |  | 6/2000 |
| JP | 2000175889 |  | 6/2000 |
| JP | 2000-237172 | | 9/2000 |
| JP | 2002-143132 | | 5/2002 |
| JP | 2004057489 |  | 2/2004 |
| WO | 01/41642  |   | 6/2001 |

* cited by examiner

PUNCTURE INSTRUMENT, PUNCTURE NEEDLE CARTRIDGE, PUNCTURE INSTRUMENT SET, AND PUNCTURE NEEDLE DISPOSAL INSTRUMENT

CLAIM OF PRIORITY

This application claims priority under 35 USC 371 to International Application No. PCT/JP2004/011301, filed on Jul. 30, 2004, which claims priority to Japanese Patent Application No. 2003-283328, filed on Jul. 31, 2003 and Japanese Patent Application No. 2003-316865, filed on Sep. 9, 2003, the entire contents of which are hereby incorporated by reference.

TECHNICAL FIELD

The present invention relates to a puncture instrument, a puncture needle cartridge, a puncture instrument set, and a puncture needle disposal instrument, which are used for collection of blood when measuring blood sugar or the like.

BACKGROUND ART

A diabetic patient measures blood sugar level several times a day by himself. In a hospital, blood sugar levels of diabetic patients are measured several tens of times a day. During the measurement, it is necessary to collect a small amount of blood from a fingertip or the like. Therefore, conventionally, a disposable puncture needle 1706 having a needle part 1705 as shown in FIG. 17(*a*) is attached to a puncture instrument 1700 as shown in FIG. 16, and a fingertip or arm is punctured with the puncture needle 1706, and blood collected from the punctured region is used for measurement.

The general puncture instrument 1700 comprises a cylindrical body 1701, and a cap 1713. The cylindrical body 1701 is provided with a first spring 1703 for projecting the attached puncture needle 1706, a second spring 1704 for backing the projected puncture needle 1706, and a puncture button 1702 for releasing the compressed first spring 132.

The puncture instrument 1700 is used as follows. The cap 1713 is removed from the body 1701 of the puncture instrument 1700, and the puncture needle 1706 from which a plastic cover 1709 is removed as shown in FIG. 17(*a*) is attached to an elastic claw 1712 of a slider 1711 in the body 1701, and then the cap 1713 is put on the body 1701 again. Then, the first spring 1703 is compressed to make a puncture operation ready state, and thereafter, a puncture target pressing face 1707 of the cap 1713 is applied to a puncture portion to be a target of puncture such as a fingertip. When the puncture button 1702 is pressed in this state, the compressed first spring 1703 is released and thereby the puncture needle 1706 is projected, and the puncture portion is punctured by the needle part 1705 of the puncture needle 1706. After the puncture, the puncture needle 1706 is immediately moved backward by the second spring 1704. This operation enables collection of blood.

When collecting blood using the puncture instrument 1700 as described above, it is very dangerous from a hygiene viewpoint to reuse the puncture needle 1706 which has once been used for blood collection. Therefore, it is necessary to replace the puncture needle 1706 attached to the puncture instrument 1700 for next use. A removal method is as follows. Initially, the cap 1713 is removed from the body 1701 of the puncture instrument, and thereafter, the puncture needle 1706 is removed from the slider 1711.

The needle part 1705 of the used puncture needle 1706, which is removed from the puncture instrument 1700, is covered with the plastic cover 1709 for protecting the needle part 1705 as shown in FIG. 17(*a*), and then the puncture needle 1706 must be put in a special bag 1710 as shown in FIG. 17(*b*) or a box to be discarded (for example, refer to Japanese Published Patent Application 2000-237172 (Pages 3-4, FIG. 1)).

When using the conventional puncture instrument as described above, the user must take a lot of troublesome manual operation steps for handling of the puncture needle and disposal of the puncture needle after use. Therefore, the user is apt to use the puncture needle attached to the puncture instrument several times without replacing the puncture needle at each puncture operation and blood collection.

It must be avoided from a hygiene viewpoint to use one puncture needle plural times, especially, to use one puncture needle for two or more persons. Although such situation may occur in, for example, a doctor's office or a hospital, a case where a child uses the puncture needle by mistake cannot be excluded.

Further, since the puncture needle is fabricated as a disposable one, the tip thereof becomes duller soon by plural times of uses, continuous use of the puncture needle gives severe pain to the patient.

Furthermore, in the conventional constructions of the puncture needle 1706 and the puncture instrument 1700, when attaching or detaching the puncture needle 1706, a lot of troublesome manual operation steps must be carried out, leading to a risk that the patient cannot correctly attach or detach the puncture needle 1706, and a fear that the patient may get hurt by mistake with the needle 1705 of the puncture needle 1706 during operation of attaching or detaching thereof.

When performing the puncture operation, the puncture needle 1706 attached to the puncture instrument 1700 goes back to the initial position immediately after it is moved or displaced toward the puncture target portion (puncture portion) of the patient's body. However, if the puncture needle 1706 is operated under the state where it is not correctly attached to the puncture instrument 1700, the puncture needle 1700 does not correctly operate, resulting in a risk that the patient may get hurt.

There is another conventional puncture instrument which contains plural puncture needles inside, and performs puncture operation by using these needles separately in order. In this instrument, a puncture needle after puncturing can be separately removed from the apparatus. Further, there is a driving means for moving a puncture needle backward and forward, which utilizes an elastic force of a plate spring attached to the puncture needle (for example, refer to U.S. Pat. No. 4,794,926 (pages 3-4, FIG. 1)).

However, automatic replacement of puncture needles using such puncture needle magazine is difficult to be realized in a system where the puncture needle 1706 is closely attached to the slider 1711 to slide the puncture needle forward and backward, like the conventional device shown in FIG. 17. Further, in the case of the system shown in FIG. 17, the needle portion of the puncture needle must be provided with a part for enforcing connected between the puncture needle and the slider 1711. If the above-mentioned puncture needle magazine is used as puncture needles in such construction, the size of the puncture instrument itself is undesirably increased.

Furthermore, in the conventional puncture instrument 1700, when replacing the puncture needle 1706, it is troublesome to discard the puncture needle 1706 every time the puncture needle 1706 is replaced, in addition to that the user must take a lot of troublesome manual operation steps. That is, in the conventional instrument, after the puncture needle 1706 is removed from the puncture instrument 1700 as described above, the user should store the used puncture needle 1706' in a bag or box 1710, and carry it to a hospital or discard it safely as a burnable waste by himself.

The process of replacing the puncture needle 1706 is particularly troublesome for a patient who is visually handicapped due to complication associated with diabetes.

The present invention is made to solve the above-mentioned problems and has for its object to provide a puncture instrument, a puncture needle cartridge, and a puncture instrument set which can perform continuous puncturing by a simple operation, and have small volume and high safety, and also provide a puncture needle disposal instrument which can easily remove a puncture needle from the puncture instrument by a simple operation to discard it.

DISCLOSURE OF THE INVENTION

In order to solve the above-mentioned problems, a puncture instrument described in the present invention is a puncture instrument which houses a plurality of puncture needles for puncturing the surface of a biologic body and can perform puncture operation continuously, the puncture instrument including a puncture needle cartridge for holding the plural puncture needles in a state where the puncture needles are connected in series in an axis direction of the puncture instrument.

Therefore, the puncture operation can be continuously carried out without loading a puncture needle at each puncture operation.

Further, in the puncture instrument described in the present invention, the puncture needle cartridge holds each of the respective puncture needles in such a manner that a front end of the puncture needle is protected by a portion of another puncture needle which is positioned at a rear end of the puncture needle.

Therefore, the plural puncture needles can be hygienically deployed.

Further, in the puncture instrument described in the present invention, the puncture needle comprises a needle part, and an elastic deformation member, and the puncture needle cartridge holds each puncture needle in a state where a front end of the puncture needle is protected by an elastic deformation member of another puncture needle which is positioned at a rear end of the puncture needle.

Therefore, the puncture needles can be sent orderly by only a pulling operation, without providing a puncture needle sending mechanism in the puncture needle cartridge.

Further, in the puncture instrument described in the present invention, the puncture needle cartridge is disposed in a cylindrical case, and comprises a puncture needle cartridge stopping member for stopping the puncture needle cartridge in a predetermined position in an axis direction of the case, a biasing member for biasing the puncture needle cartridge in one direction in the case, and a puncture button for dissolving the state where the puncture needle cartridge is biased by the biasing member in the one direction, to start a puncture operation.

Therefore, it is possible to provide a puncture instrument which contains, in its body, a puncture needle cartridge loaded with plural puncture needles, and performs puncture action continuously by simple operation.

Further, the puncture instrument described in the present invention further includes a remaining quantity check means for checking the remaining quantity of the plural puncture needles in the puncture needle cartridge.

Therefore, it is possible to immediately check the number of puncture needles loaded in the puncture instrument, or the number of used puncture needles.

Further, in the puncture instrument described in the present invention, the remaining quantity check means has, on a side surface of the puncture instrument, a puncture needle remaining quantity check window through which the puncture needles existing in the puncture needle cartridge can be visually checked.

Therefore, it is possible to visually and immediately check the number of puncture needles loaded in the puncture instrument.

Further, in the puncture instrument described in the present invention, the puncture needle cartridge is detachably provided in the puncture instrument.

Therefore, it becomes possible to perform replacement of puncture needles, with the plural puncture needles being loaded in the cartridge, whereby loading of the plural puncture needles can be reliably carried out.

Further, according to the present invention, there is provided a puncture needle cartridge which contains a plurality of puncture needles for puncturing the surface of a biologic body, and is housed in a puncture instrument that is able to perform puncture operations continuously, wherein the puncture needle cartridge holds the plural puncture needles in a state where the puncture needles are connected in series in an axis direction of the puncture instrument.

Therefore, it is possible to deploy a lot of puncture needles in the instrument so as to be connected to each other, without the necessity of loading a puncture needle individually for each puncturing, whereby the puncture operation can be continuously carried out.

Further, in the puncture needle cartridge described in the present invention, a front end of each of the plural puncture needles is fitted to a portion of another puncture needle which is positioned at a rear end of the puncture needle.

Therefore, the plural puncture needles can be used hygienically, and the volume of the plural puncture needles can be reduced, whereby a greater number of puncture needles can be loaded in the puncture needle cartridge.

Further, in the puncture needle cartridge described in the present invention, each of the plural puncture needles comprises a needle part, and an elastic deformation member, and a front end of each puncture needle is fitted to an elastic deformation member of another puncture needle which is positioned at a rear end of the puncture needle.

Therefore, the puncture needles can be sent orderly by only pulling operation, without providing a puncture needle sending mechanism.

Further, the puncture needle cartridge described in the present invention further includes puncture needle stopping members for holding the respective puncture needles at predetermined positions in the puncture needle cartridge.

Therefore, the puncture operation can be reliably carried out.

Further, in the puncture needle cartridge described in the present invention, the puncture needle stopping members are provided in the puncture needle cartridge at a regular interval that is approximately equal to the length of the puncture needle.

Therefore, plural puncture needles can be loaded in the puncture needle cartridge such that the puncture needles are arranged at the same pitch in the longitudinal direction.

Further, in the puncture needle cartridge described in the present invention, the fitting strength between the respective puncture needles is larger than a load which is applied to the puncture needle when the holding of the puncture needle by the puncture needle stopping member that holds the puncture needle at the predetermined position in the puncture needle cartridge is dissolved.

Therefore, it is possible to naturally and reliably carry out the operation of pulling a puncture needle that has finished the puncture operation, thereby to send a next puncture needle which is located at the rear end of the pulled puncture needle, directly to its puncture position.

Further, the puncture needle cartridge described in the present invention further includes a puncture needle retaining elastic member for holding a puncture needle positioned at the head of the puncture needle cartridge to prevent escape and dropout of the puncture needle from the puncture instrument body.

Therefore, the puncture operation can be carried out safely and reliably.

Further, in the puncture needle cartridge described in the present invention, the puncture needle retaining elastic member is integrated with the puncture cartridge.

Therefore, it is possible to provide a puncture needle cartridge which can reliably prevent escape and dropout of the puncture needle.

Further, in the puncture needle cartridge described in the present invention, each of the puncture needles has, at its surface, two dents which are respectively engaged with a puncture needle stopping member for holding the puncture needle in the puncture needle cartridge and engaged with a puncture needle stopping elastic member for preventing escape and dropout of the puncture needle from the puncture needle cartridge.

Therefore, the puncture needle can be reliably located and held in a predetermined position in the puncture needle cartridge.

Further, in the puncture needle cartridge described in the present invention, a puncture needle group comprising the plural puncture needles being connected in series is provided with a puncture needle cap which protects a needle part of a puncture needle that is positioned at the head of the group.

Therefore, when loading a puncture needle or a puncture needle cartridge at start of use, it can be safely loaded in the puncture instrument body.

Further, the puncture needle cartridge described in the present invention further includes a rotation stopping member which engages with the body of the puncture instrument to prevent the puncture instrument from rotating around the axis of the puncture instrument.

Therefore, the puncture needle cartridge is prevented from rotating around the axis of the puncture instrument, and the puncture needle cartridge can reliably slide only in the axis direction of the puncture instrument, whereby the puncture operation can be easily realized by only the motion of the puncture needle cartridge itself in the drive axis direction.

Further, the puncture needle cartridge described in the present invention further includes a remaining quantity check means for checking the remaining quantity of the plural puncture needles in the puncture needle cartridge.

Therefore, it is possible to immediately check the number of used puncture needles or the number of remaining puncture needles.

Further, in the puncture needle cartridge described in the present invention, the remaining quantity check means varies the respective colors of the plural puncture needles.

Therefore, it is possible to immediately determine the order from the first use of the puncture needles, or the remaining quantity of the puncture needles.

Further, in the puncture needle cartridge described in the present invention, the remaining quantity check means assigns numbers (production codes) to the respective puncture needles.

Therefore, it is possible to immediately determine the order from the first use of the puncture needles, or the remaining quantity of the puncture needles.

Further, in the puncture needle cartridge described in the present invention, when a new puncture needle is loaded in the puncture needle cartridge, a puncture needle comprising the plural puncture needles being connected in series is loaded in the puncture needle cartridge.

Therefore, the puncture needle cartridge can be integrally contained in the puncture instrument, whereby plural puncture needles can be easily loaded in the puncture instrument.

Further, in the puncture needle cartridge described in the present invention, when the puncture needle group is loaded in the puncture needle cartridge, the puncture needle group is loaded only in one direction of the puncture needle cartridge.

Therefore, puncture needles can be safely replenished.

Further, the puncture needle cartridge described in the present invention further includes an improper loading prevention return member for preventing the puncture needle group from being loaded in a wrong direction when it is loaded in the puncture needle cartridge.

Therefore, improper loading of the plural puncture needles being connected can be prevented, thereby providing a high-security puncture needle cartridge.

Further, the puncture needle cartridge described in the present invention is attachable and detachable to/from the puncture instrument.

Therefore, the puncture needle cartridge itself can be replaced, whereby loading of puncture needles can be reliably carried out at one time.

Further, according to the present invention, there is provided a puncture instrument set comprising: a puncture instrument which is provided with a puncture needle cartridge that holds a plurality of puncture needles for puncturing the surface of a biologic body, the puncture needles being connected in series in an axis direction of the cartridge, and the puncture instrument performing puncture operation continuously; and a puncture needle replacement jig which performs, after puncturing by the puncture needle, setting of the puncture needle cartridge at a puncture operation start position for a next puncture operation, and removal of the used puncture needle from the puncture needle cartridge.

Therefore, when the puncture operation is ended and the puncture needle is replaced, the used puncture needle can be detached with higher safety, and further, a next new puncture needle can be set at the puncture operation start position simultaneously with the detachment, whereby the puncture operation can be continuously carried out safely by a simpler operation.

Further, in the puncture instrument set described in the present invention, the puncture needle replacement jig includes a replacement jig return member which holds the puncture needle after puncturing, and removes the puncture needle from the puncture needle cartridge.

Therefore, the puncture needle that has finished the puncture operation can be reliably held in the puncture needle cartridge and then discarded, and further, a new puncture needle to be used next can be orderly sent to the puncture operation start position.

Further, in the puncture instrument set described in the present invention, the puncture needle replacement jig sets the puncture needle cartridge at the puncture operation start position simultaneously with removal of the puncture needle after puncturing.

Therefore, even a visually handicapped person or an elderly person can easily remove the used puncture needle, and further, set a new puncture needle to be used next to prepare for next puncturing.

Further, in the puncture instrument set described in the present invention, when the puncture needle after puncturing is removed from the puncture needle cartridge by the puncture needle replacement jig, each of the plural puncture needles connected in series in the puncture needle cartridge is moved toward a front end of the puncture needle cartridge until it is held by a puncture needle stopping member which holds each puncture needle at a predetermined position in the puncture needle cartridge.

Therefore, the user can perform the puncture action more safely by a simpler operation.

Further, the puncture instrument set described in the present invention further includes a puncture needle retaining elastic member for holding a puncture needle positioned at the head of the puncture needle cartridge to prevent escape and dropout of the puncture needle from the puncture instrument body; and the puncture needle retaining elastic member bends within an elasticity range of the puncture needle retaining elastic member due to fitting of the elastic member to a front end portion of the puncture needle replacement jig, whereby holding of the puncture needle positioned at the head of the puncture needle cartridge is dissolved.

Therefore, holding of the used puncture needle in the puncture needle cartridge can be easily dissolved, thereby reliably preparing for a next puncture operation.

Further, in the puncture instrument set described in the present invention, the puncture instrument is provided with a remaining quantity check means for checking the remaining quantity of the plural puncture needles in the puncture needle cartridge.

Therefore, it is possible to easily check the number of puncture needles remaining in the puncture instrument or the number of used puncture needles.

Further, according to the present invention, there is provided a puncture instrument set comprising: a puncture instrument which is provided with a puncture needle cartridge that holds a plurality of puncture needles for puncturing the surface of a biologic body, the puncture needles being connected in series in an axis direction of the cartridge, and the puncture instrument performing puncture operation continuously; and a puncture needle disposal instrument which performs, after puncturing by the puncture needle, setting of the puncture needle cartridge at a puncture operation start position for a next puncture operation, removal of the used puncture needle from the puncture needle cartridge, and storage of the removed puncture needle to be discarded.

Therefore, by the operation of only inserting and removing the disposal instrument in/from the puncture instrument, the used puncture needles can be safely and easily removed from the puncture instrument and the plural used puncture needles can be safely stored, and simultaneously, a next new puncture needle can be set at the puncture operation start position to prepare for a next puncture operation.

Further, in the puncture instrument set described in the present invention, the puncture needle disposal instrument comprises a disposal instrument return member for holding the used puncture needle, and removing the used puncture needle from the puncture instrument; and a cylindrical member which can store a plurality of the removed puncture needles to be discarded.

Therefore, a plurality of used puncture needles can be stored at one time, whereby the safety at disposal or the like of the puncture needles can be enhanced.

Further, in the puncture instrument set described in the present invention, the puncture needle disposal instrument comprises a disposal instrument return member for holding the used puncture needle, and removing the used puncture needle from the puncture instrument, a cylindrical member which can store a plurality of the removed puncture needles to be discarded, and a disposal box having an opening into which the cylindrical member is inserted, the disposal box capable of storing the plural puncture needles to be discarded.

Therefore, by the operation of only inserting and removing the disposal instrument in/from the puncture instrument, the puncture needle can be safely and easily removed from the puncture instrument, and more puncture needles removed can be stored safely. Further, there is no fear that the puncture needles stored in the disposal box get out of the disposal box when discarding the disposal box, thereby enhancing the safety.

Further, according to the present invention, there is provided a puncture needle disposal instrument for removing, from a puncture instrument having a holding member which detachably holds a puncture needle for puncturing the surface of a biologic body, the puncture needle to discard the same, the instrument comprising a disposal instrument return member for holding the used puncture needle and removing the puncture needle from the puncture instrument, and a cylindrical member which stores a plurality of the removed puncture needles to be discarded.

Therefore, the puncture needles can be safely and easily removed from the puncture needle instrument by the operation of only inserting and removing the disposal instrument in/from the puncture instrument, and the plural puncture needles removed can be safely stored.

Further, in the puncture needle disposal instrument described in the present invention, a front end of the cylindrical member is closed to prevent the disposal puncture needles stored in the cylindrical member from getting out of the cylindrical member.

Therefore, there is no fear that the puncture needles stored in the disposal box get out of the box when discarding the disposal box, thereby enhancing the safety.

Further, according to the present invention, there is provided with a puncture needle disposal instrument for removing, from a puncture instrument having a holding member which detachably holds a puncture needle for puncturing the surface of a biologic body, the puncture needle to discard the same, the instrument comprising a disposal instrument return member for holding the used puncture needle and removing the puncture needle from the puncture instrument, a cylindrical member which stores a plurality of the removed puncture needles to be discarded, and a disposal box having an opening into which the cylindrical member is inserted, the disposal box capable of storing the plural puncture needles to be discarded.

Therefore, the puncture needles can be safely and easily removed from the puncture instrument by the operation of only inserting and removing the disposal instrument in/from the puncture instrument, and plural puncture needles removed can be safely stored.

Further, in the puncture needle disposal instrument described in the present invention, the cylindrical member and the disposal box are separable from each other.

Therefore, when discarding the puncture needles, only the disposal box is discarded, and the cylindrical member can be recycled.

Further, in the puncture needle disposal instrument described in the present invention further includes a means for closing the opening of the disposal box when the cylindrical member and the disposal box are separated from each other.

Therefore, when discarding only the disposal box, there is no fear that the puncture needles stored in the disposal box get out of the box, thereby enhancing the safety.

Further, in the puncture needle disposal instrument described in the present invention, the whole or a portion of the cylindrical member is transparent.

Therefore, it is possible to immediately check the state of storage of the used puncture needles in the cylindrical part.

Further, in the puncture needle disposal instrument described in the present invention, the whole or portions of the cylindrical member and the disposal box is transparent.

Therefore, it is possible to immediately check the state of storage of the used puncture needles in the disposal box or the like.

Further, the puncture needle disposal instrument described in the present invention further includes a member for guiding the outer shape of the front end portion of the puncture instrument, at the upper surface of the opening of the disposal box.

Therefore, the puncture instrument can be guided to the opening of the disposal box with higher accuracy, thereby enhancing the operability.

Further, the puncture needle disposal instrument described in the present invention includes a stopper for restricting the depth of insertion of the cylindrical member into the opening of the disposal box, the stopper being disposed in the vicinity of the opening of the disposal box.

Therefore, when the puncture instrument to which the member for removing the puncture needle from the puncture instrument is attached is inserted into the puncture needle disposal instrument, it is possible to prevent that the front end of the puncture needle removal member excessively enters the opening of the disposal box, or that a large stress is applied to the puncture needle removal member to lead the stress being applied to the inside of the puncture instrument through the puncture needle body.

BEST MODE TO EXECUTE THE INVENTION

Hereinafter, embodiments of the present invention will be described with reference to the drawings.

Embodiment 1

Figure 1:
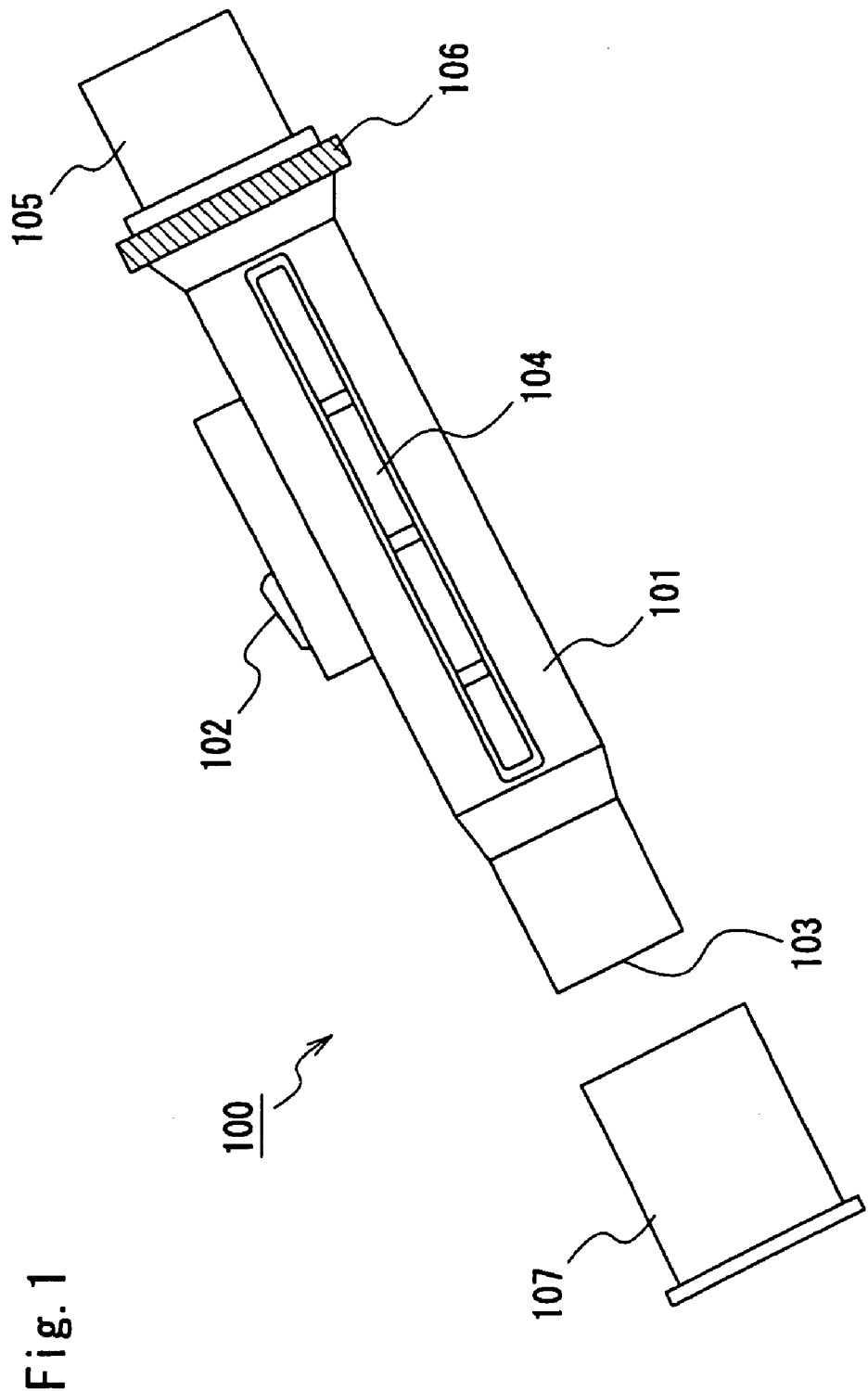
FIG. 1 is an outline view of a puncture instrument set according to a first embodiment of the present invention.

FIG. 1 is an external view of a puncture instrument set which can perform continuous puncture operation, according to a first embodiment of the present invention.

With reference to FIG. 1, the puncture instrument set 100 according to the first embodiment is provided with a puncture instrument 101 for performing puncturing, and a puncture needle replacement jig 107. The puncture needle replacement jig 107 removes a puncture needle that is held in the puncture instrument, and simultaneously, sets a next new puncture needle in a puncture operation start position.

The puncture instrument 101 comprises a puncture button 102 for starting the puncture operation, a puncture portion pressing plane 103 to be applied to a puncture target portion (hereinafter referred to as "puncture portion") such as a finger of a user, remaining quantity check window 104 for checking the number of remaining puncture needles, a rear end cap 105, and a puncture depth adjuster 106 for controlling the puncture depth. The puncture instrument 101 contains a puncture needle cartridge which holds plural puncture needles in a state where the needles are connected in series along the axis direction of the puncture instrument 101.

Hereinafter, the puncture needle cartridge and the puncture needles loaded into the puncture needle cartridge will be described with reference to FIGS. 2 and 3.

Figure 2:
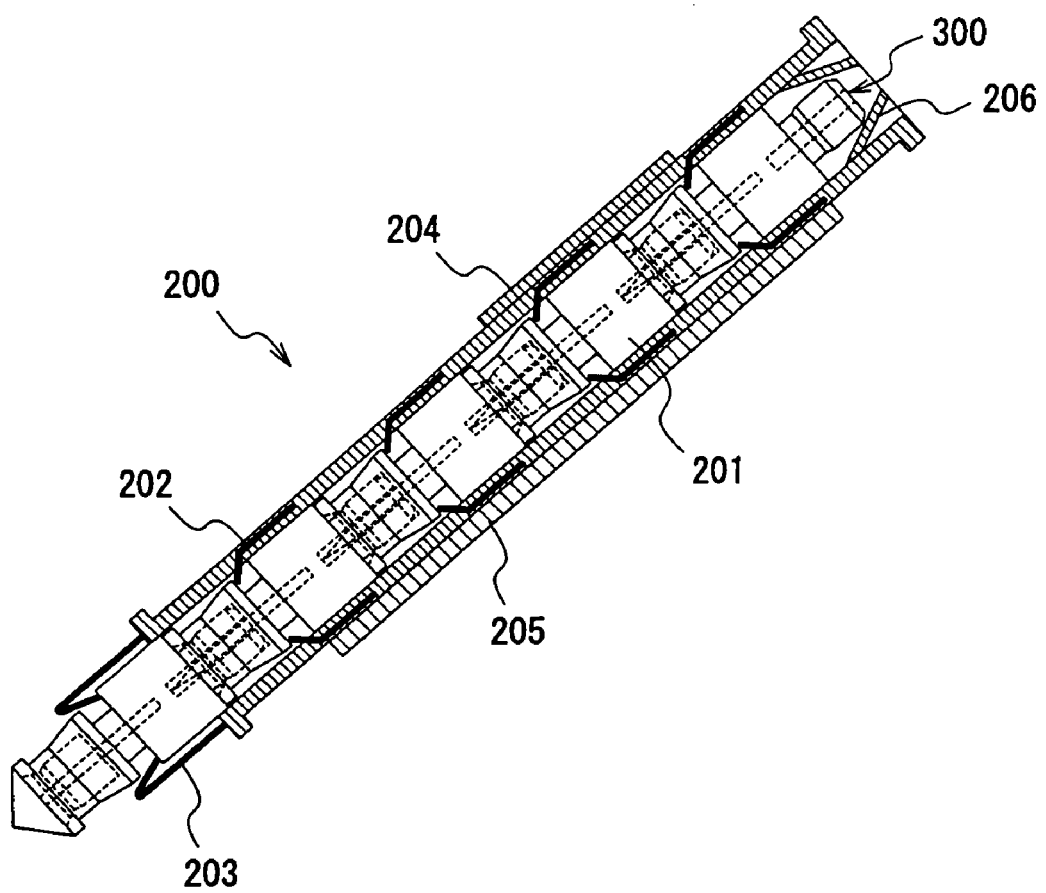
FIG. 2 is a cross-sectional view illustrating the construction of a puncture needle cartridge according to the first embodiment of the present invention.

FIG. 2 is a cross-sectional view of the puncture needle cartridge in which puncture needles are loaded, which cartridge is embedded in the puncture instrument 101 of the first embodiment.

With reference to FIG. 2, the puncture needle cartridge 200 holds a puncture needle group 300 in which plural puncture needles 201 are connected, and comprises puncture needle stopping members 202, a puncture needle retaining elastic member 203, a set claw engaging part 204, a cartridge rotation stopper 205, and an improper loading prevention return member 206.

Each puncture needle stopping member 202 holds each of the plural puncture needles 201 (five needles) at a predetermined position in the puncture needle cartridge 200. The puncture needle stopping members 202 comprise elastic members such as plate springs, and are placed in the puncture needle cartridge 200 at a regular interval that is approximately equal to the length of the puncture needle 201. The puncture needle retaining elastic member 203 comprises an elastic member such as a plate spring, and it is united with the puncture needle cartridge 200 at a front end of the puncture needle cartridge in order to prevent escape or dropout of the puncture needle 201 from the puncture needle cartridge 200. The set claw engaging part 204 is engaged with an end of the puncture button 102 of the puncture instrument 101 to maintain the puncture needle cartridge 200 at a puncture operation start position. The cartridge rotation stopper 205 engages the body of the puncture instrument with the puncture needle cartridge 200 to prevent rotation of the cartridge in the direction of the circumference of the puncture instrument, when the puncture needle cartridge 200 operates in the puncture instrument. The improper loading prevention return member 206 comprises an elastic member which is elastically displaceable, and prevents the puncture needle 201 from being loaded in a wrong direction when loading the puncture needle 201 in the puncture needle cartridge 200.

Figure 3A:
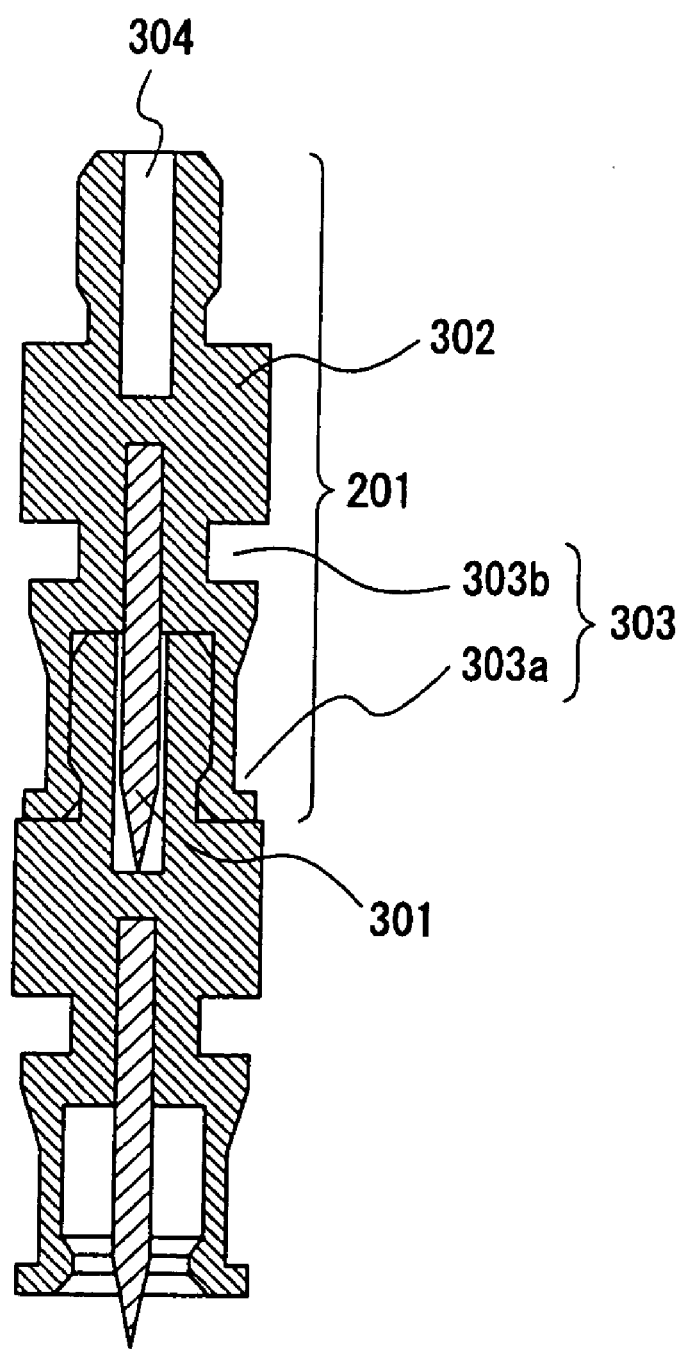
FIG. 3(a) is an enlarged cross-sectional view of a puncture needle according to the first embodiment of the present invention.
Figure 3B:
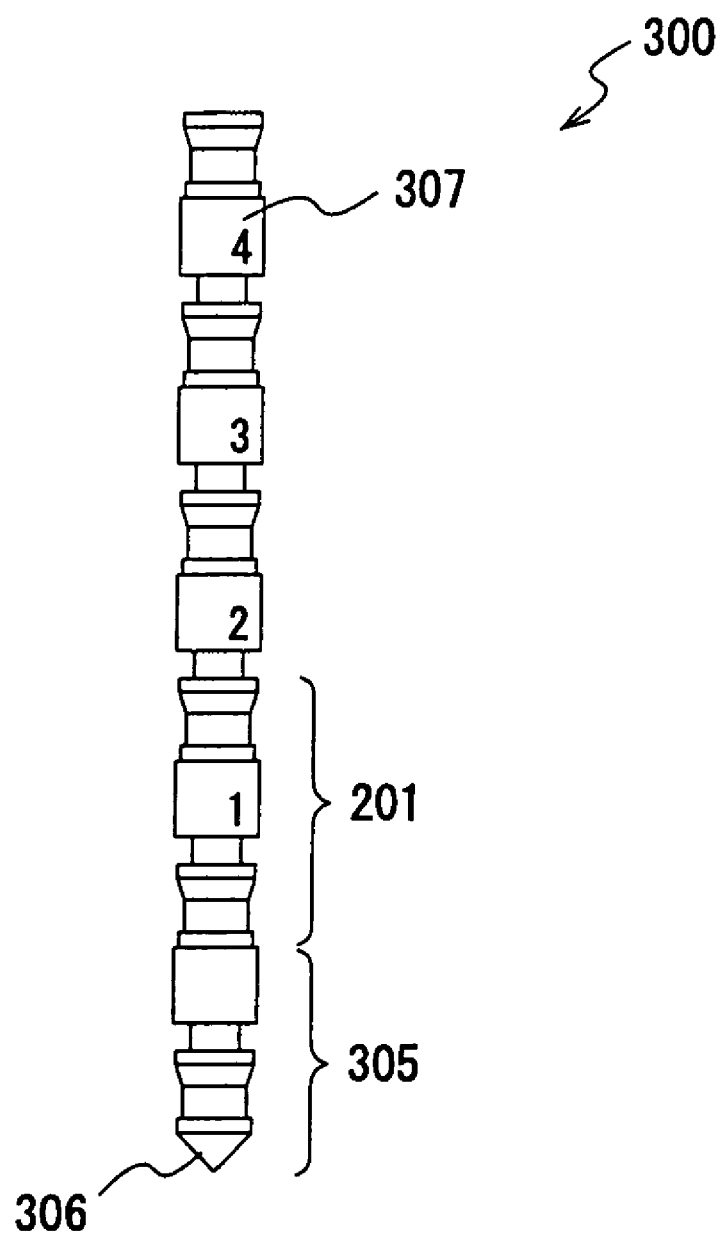
FIG. 3(b) is an outline view of a puncture needle group comprising puncture needles being connected, according to the first embodiment of the present invention.

FIG. 3 is a diagram for explaining the puncture needles. FIG. 3(a) is a enlarged cross-sectional view of the puncture needles, and FIG. 3(b) is a diagram illustrating the state of a puncture needle group comprising a predetermined number of puncture needles being connected, before being loaded into the puncture needle cartridge.

As shown in FIG. 3(a), each puncture needle 201 comprises a needle part 301 and an elastic deformation part 302, which are united in one body. The elastic deformation part 302 of each puncture needle 201 is shaped such that a rear end thereof is fitted to a front end of a next puncture needle, and further, the rear end of the puncture needle 201 is provided with a hole 304 into which a needle portion 301 of the next puncture needle is inserted. Thereby, the respective puncture needles 201 can be successively connected to be united in one body, and the needle portion 301 of each puncture needle 201 can be generally kept clean, and further, the volume of the puncture needle group 300 can be reduced.

The fitting strength between the rear end of each puncture needle 201 and the front end of the next puncture needle should be secured so that the serial connection of the puncture needles is not disconnected even when a load is applied from the puncture needle stopping member 202 to the puncture needles 201. The fitting strength of the puncture needle 201 can be controlled by controlling the shape and size of the elastic deformation member 302 of each puncture needle 201.

Further, the elastic deformation part 302 of each puncture needle 201 has dents 303a and 303b. Each puncture needle 201 is held by the puncture needle cartridge 200 when the puncture needle stopping member 202 of the puncture needle cartridge 200 is engaged into the dent 303b. Further, replacement of the puncture needle is enabled when a replacement jig return member of a puncture needle replacement jig 107 to be described later is engaged into the dent 303a.

The puncture needle group 300 comprising a predetermined number of puncture needles 201 which are connected and united as mentioned above is, as shown in FIG. 3(b), loaded into the puncture needle cartridge 200, with a puncture needle head cap 305 being connected to the front end of the puncture needle group 300. When the user loads the puncture needle group 300 into the puncture needle cartridge 200, the cap 305 enables the user to perform the operation safely. Further, an improper loading prevention front end part 306 is disposed at the front end of the puncture needle cap 305. When loading the puncture needle group 300 into the puncture needle cartridge 200, the improper loading prevention front end part 306 inhibits loading of the puncture needle group 300 into the cartridge 200 unless the loading operation is carried out from the side of the puncture needle head cap 305 disposed at the head of the puncture needle group 300, thereby preventing the user from loading the puncture needle group 300 into the puncture needle cartridge 200 in the wrong loading direction.

Hereinafter, a description will be given of the operation of loading the puncture needle group 300 into the puncture needle cartridge 200. Initially, the rear end cap 105 disposed at the rear of the puncture instrument 101 is removed. Thereby, the rear end of the puncture needle cartridge 200 embedded in the puncture instrument 101 is exposed. The puncture needle group 300 in which plural puncture needles 201 are connected as shown in FIG. 3(b) is inserted into the puncture needle cartridge 200 from the side of the puncture needle head cap 305. At this time, the puncture needle group 300 is pressed into the puncture needle cartridge 200 while broadening the improper loading prevention return member 206 of the puncture needle cartridge 200 by the improper loading prevention front end part 306. Then, the puncture needle group 300 is continuously pressed into the puncture needle cartridge 200 by hand, and finally, the loading operation is finished when the puncture needle retaining elastic member 203 is engaged into the dent 303b of the puncture needle head cap 305 as shown in FIG. 2.

When the loading operation of the puncture needle group 300 is ended, the respective puncture needles 201 are held by the respective puncture needle stopping members 202 provided in the puncture needle cartridge 200 as shown in FIG. 2. To be specific, the front end of each puncture needle stopping member 202 is slightly bent toward the center axis of the puncture needle cartridge 200, and the bent front end of the puncture needle stopping member 202 is engaged into the dent 303b of each puncture needle 201, whereby each puncture needle 201 is held in the puncture needle cartridge 200.

The rear end cap 105 is closed after the puncture needle group 300 is inserted into the puncture needle cartridge 200 as described above, thereby completing the operation of loading the puncture needle group 300 into the puncture needle cartridge 200. At this time, the puncture needle cartridge 200 is in the state where the rear end of the cartridge 200 is held by the puncture needle cartridge stopping part 402.

Figure 4:
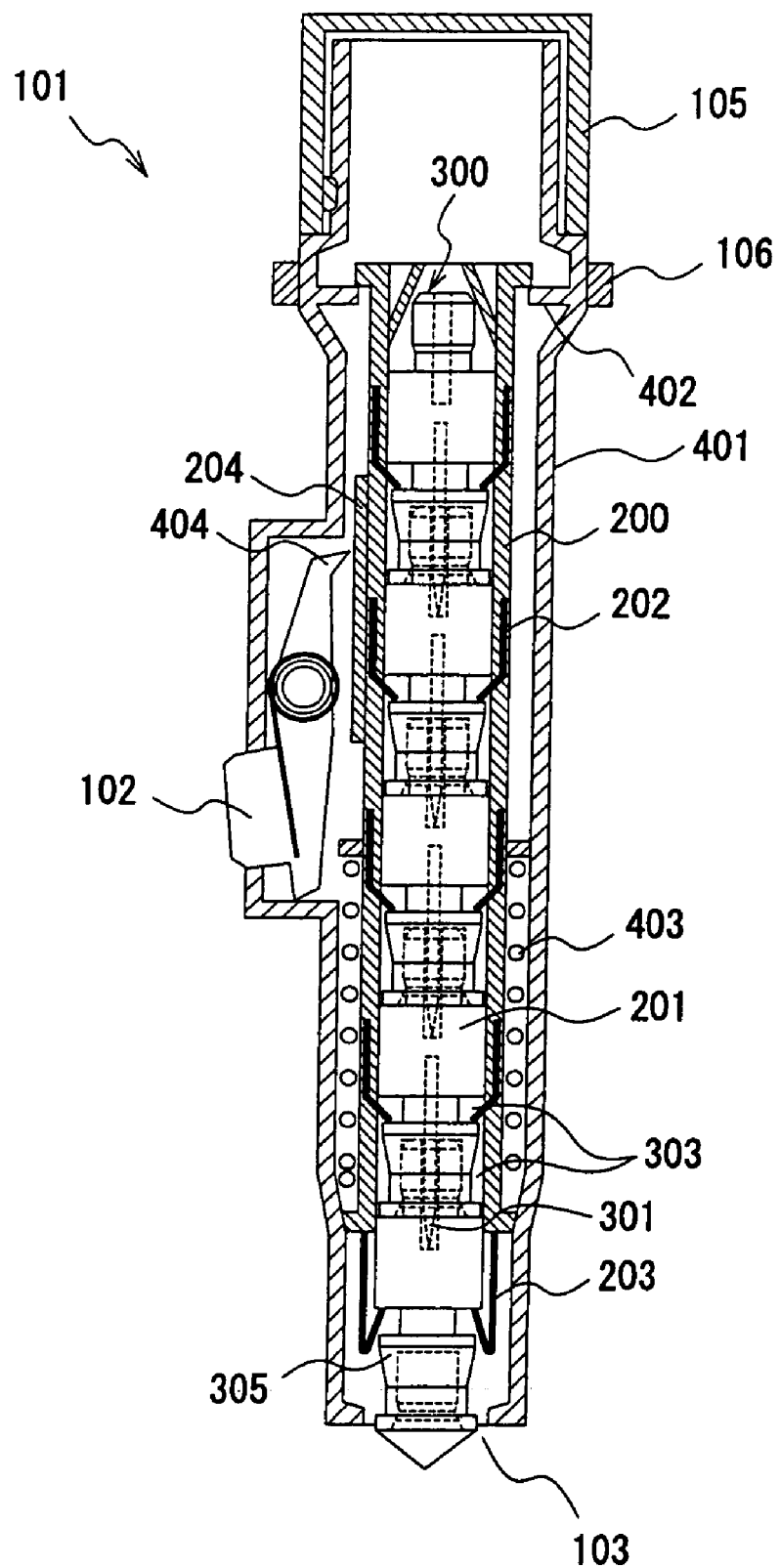
FIG. 4 is a cross-sectional view of a puncture needle in which a puncture needle cartridge is loaded, according to the first embodiment of the present invention.

FIG. 4 is a cross-sectional view of the puncture instrument 101 in which the puncture needle group 300 is attached into the puncture needle cartridge 200. The puncture needle cartridge 200 is embedded in the body 401 of the puncture instrument 101, and the body 401 is provided with a puncture needle cartridge stopping part 402, a biasing member 403 comprising an elastic member, a set claw 404 as an end of the puncture button 102, and a rotation stopper support (not shown).

The puncture needle cartridge stopping part 402 stops the puncture needle cartridge 200 at a predetermined position, which cartridge 200 moves in the body 401 of the puncture instrument 101 in its axis direction. The position of the puncture needle cartridge stopping part 402 is adjustable in the longitudinal direction of the puncture instrument 101 by the puncture depth adjuster 106. The puncture depth of the puncture needle 201 can be varied by adjusting the position of the puncture needle cartridge stopping part 402. The puncture depth adjuster 106 can be implemented by such as a sliding mechanism, and alternatively, it can be implemented by a spring mechanism that is attached to a ring-shaped member engaged with the puncture needle cartridge stopping part 402.

The biasing member 403 biases the puncture needle cartridge 200 toward the puncture portion pressing plane 103 that is the front end of the puncture instrument 101, and a compression spring is employed as an example of the biasing member 403 in this first embodiment. The set claw 404 stops the set claw engaging part 204 of the puncture needle cartridge 200 so that the puncture needle cartridge 200 can maintain the puncture operation start position in the puncture instrument 101.

The rotation stopper support (not shown) is provided at the inner wall of the body 401 of the puncture instrument 101, and is engaged with the cartridge rotation stopper 207 of the puncture needle cartridge 200, whereby the puncture needle cartridge 200 slides only in the axis direction, without rotating in the direction of the circumference of the puncture instrument 101.

Figure 6:
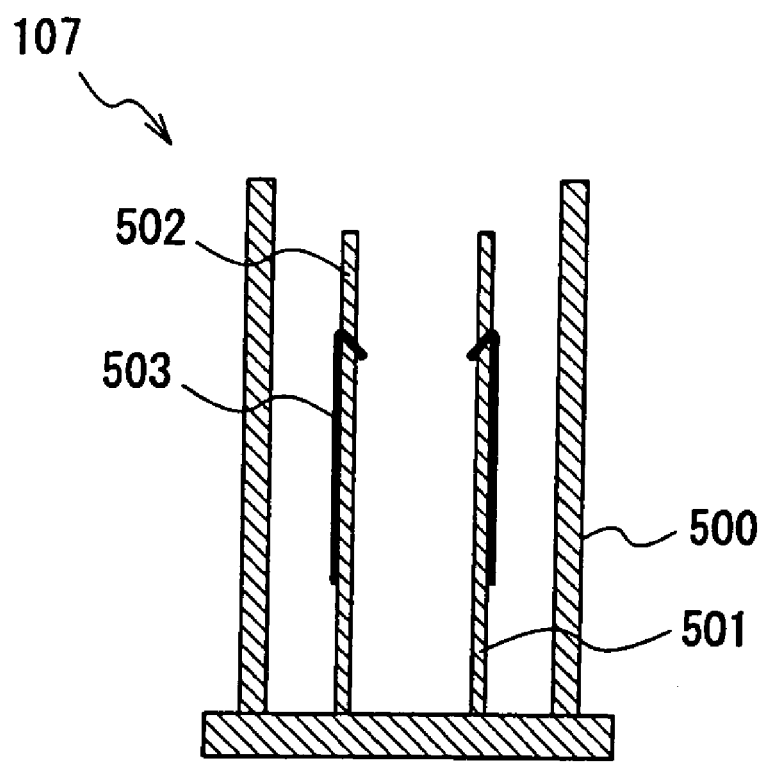
FIG. 6 is a cross-sectional view of the puncture needle replacement jig of the puncture instrument set according to the first embodiment of the present invention.

FIG. 6 is a cross-sectional view illustrating the construction of a puncture needle replacement jig of the puncture instrument set 100 according to the first embodiment.

The puncture needle replacement jig 107 has a double cylindrical structure comprising an outer cylinder 500 and an inner cylinder 501. An end of the inner cylinder 501 functions as a replacement jig pressing part 502 for releasing holding of the puncture needle by the puncture needle retaining elastic member 203 of the puncture needle cartridge 200. Further, as shown in FIG. 5, the replacement jig pressing part 502 of the inner cylinder 501 is provided with a replacement jig return member 503 which is engaged into the dent 303a of the puncture needle 201 in the puncture needle cartridge 200 to hold the puncture needles 201 one by one.

Next, the puncture operation of the puncture instrument according to the first embodiment of the present invention will be described with reference to FIGS. 4 to 6.

Initially, the puncture needle cartridge 200 in the puncture instrument 101 is set at the puncture operation start position.

Figure 5:
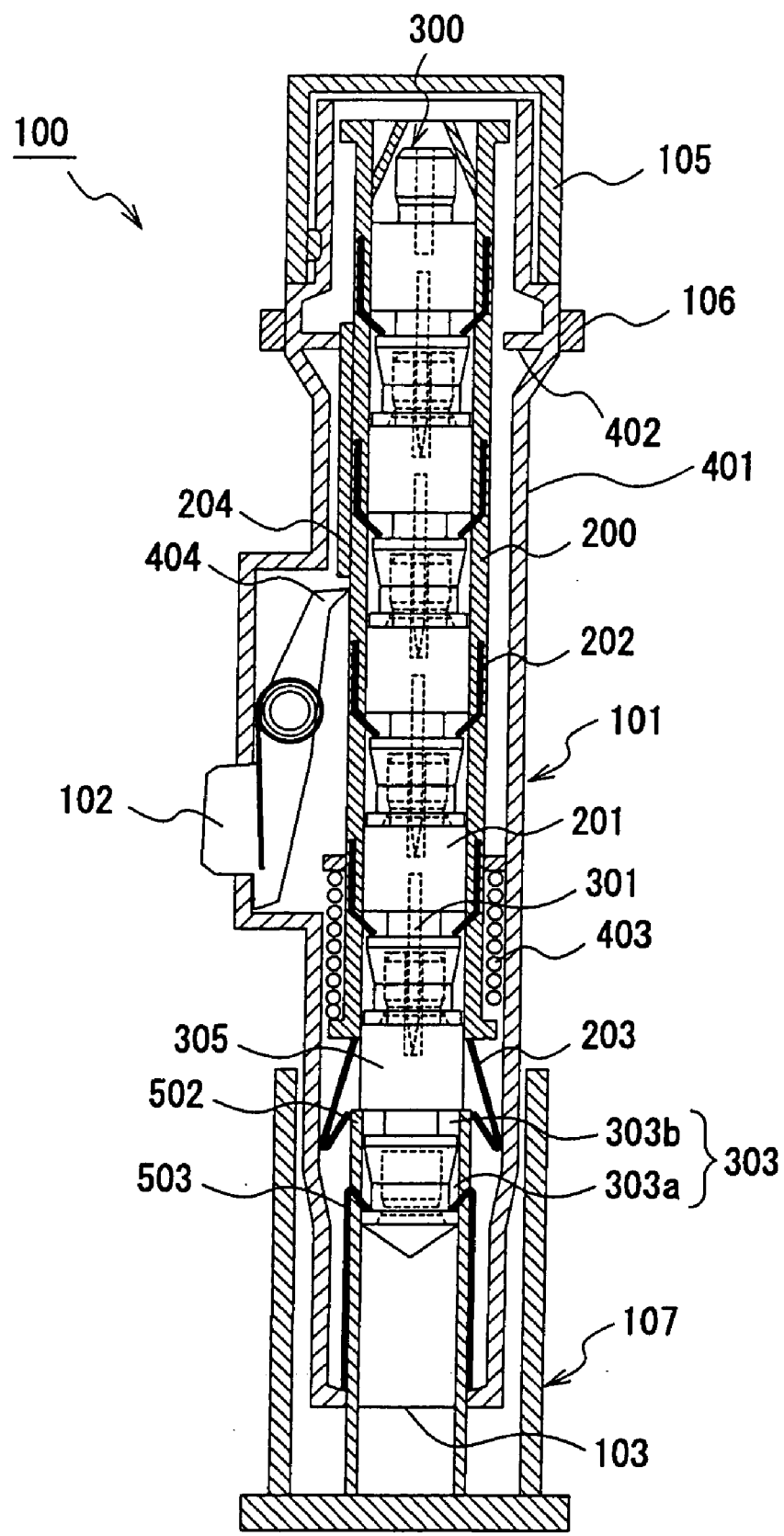
FIG. 5 is a cross-sectional view for explaining replacement of puncture needles using a puncture needle replacement jig, in the puncture instrument set according to the first embodiment of the present invention.

FIG. 5 is a diagram illustrating the operation of setting the puncture instrument 101 at the puncture operation start position.

Setting of the puncture instrument 101 at the puncture operation start position is performed by inserting the puncture needle replacement jig 107 from the puncture portion pressing plane of the puncture instrument 101, as shown in FIG. 5.

Hereinafter, the operation of setting the puncture needle cartridge 200 at the puncture operation start position will be described in more detail.

Initially, the puncture needle replacement jig 107 is inserted from the puncture portion pressing plane 103 into the puncture instrument 101 in the state shown in FIG. 4, whereby the replacement jig pressing part 502 of the puncture needle replacement jig 107 pushes the puncture needle retaining elastic member 203 of the puncture instrument 101 to dissolve the state where the puncture needle retaining elastic member 203 is engaged with the dent 303b of the puncture needle 201, as shown in FIG. 5. When the puncture needle replacement jig 107 is further inserted, the replacement jig return part 503 of the puncture needle replacement jig 107 elastically bends, and thereafter, it is engaged into the dent 303a of the puncture needle 201. Thereby, the puncture needle replacement jig 107 holds the puncture needle head cap 305 of the puncture needle cartridge 200.

Thereafter, when the puncture needle replacement jig 107 is further inserted, the replacement jig pressing part 502 pushes up the puncture needle retaining elastic member 203 of the puncture needle cartridge 200 while moving against the reaction force of the biasing member 403 of the puncture instrument 101, whereby the whole puncture needle cartridge 200 is moved to the rear end side of the body 401 of the puncture instrument 101. Finally, as shown in FIG. 5, the puncture needle replacement jig 107 is pressed to push up the puncture needle cartridge 200 until the set claw engagement part 204 disposed at the surface of the puncture needle cartridge 200 is engaged with the set claw 204 disposed at an end of the puncture button 102 of the puncture instrument 101.

When the set claw engagement part 204 is stopped by the set claw 404, the puncture needle cartridge 200 does not move back to the initial position (FIG. 4) again due to the return force of the biasing member 403, whereby the puncture needle cartridge 200 can be set at the puncture operation start position.

Thereafter, the puncture needle replacement jig 107 is pulled out of the puncture instrument 101, whereby the puncture needle head cap 305 which is held by the replacement jig return member 503 of the puncture needle replacement jig 107 is pulled out of the puncture needle cartridge 200 together with the puncture needle replacement jig 107, and the new puncture needle 201 positioned in the rear stage of the puncture needle head cap 305 is surely sent forward to the head of the puncture needle group 300.

Figure 7:
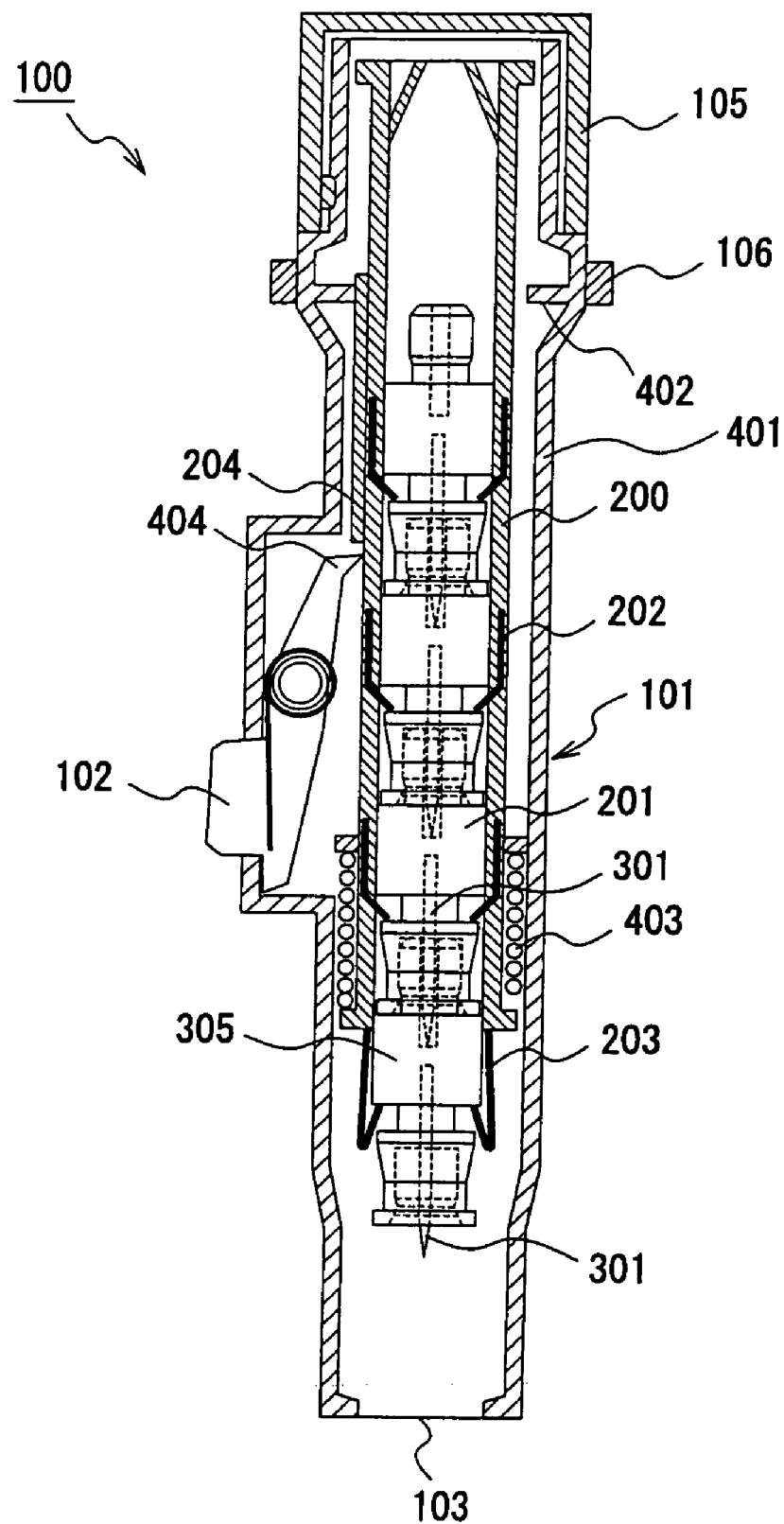
FIG. 7 is a diagram illustrating a state where the puncture needle cartridge of the puncture instrument is set at a puncture operation start position, according to the first embodiment of the present invention.

Then, in the puncture instrument 100 in the state shown in FIG. 7, when the operation of pressing the puncture button 102 is carried out, the engagement between the set claw 404 and the set claw engagement part 204 is dissolved, and the puncture needle cartridge 200 moves linearly on the axis line of the puncture instrument 101 from the puncture operation start position due to the return force of the biasing member 403, whereby the needle part 301 of the puncture needle 201 reaches the puncture portion pressing plane 103 of the puncture instrument 101 at a dash, with the puncture needle 201 being fixed in the puncture needle cartridge 200. Further, the puncture needle 201 passes through the puncture portion pressing plane 103 while being held by the puncture needle retaining elastic member 203, and thereafter, the puncture needle 201 goes back to the initial position (FIG. 4) before it is set at the puncture operation start position by the return force of the biasing member 403, thereby completing a series of puncture operations.

When a next puncture operation is carried out after the above-mentioned puncture operation has ended, the puncture needle replacement jig 107 is inserted into the puncture instrument 101 as described above, and the puncture needle cartridge 200 is set at the puncture operation start position and, simultaneously, the operation of removing the used puncture needle is carried out.

As described above, according to the first embodiment, a next new puncture needle 201 can be orderly sent to the front end side of the puncture needle cartridge 200 simultaneously with removal of the used puncture needle by the puncture needle replacement jig 107.

The puncture needle cartridge 200 is preferably constructed so as to be supported at plural positions not less than two in the longitudinal direction of the puncture needle 201. Thereby, blurring of the puncture needle cartridge 200 can be reduced when the puncture needle cartridge slides in the longitudinal direction in the puncture instrument, and therefore, the puncture needle cartridge 200 can be functioned as a guide member for the sliding motion of the puncture needle group 300.

Figure 8:
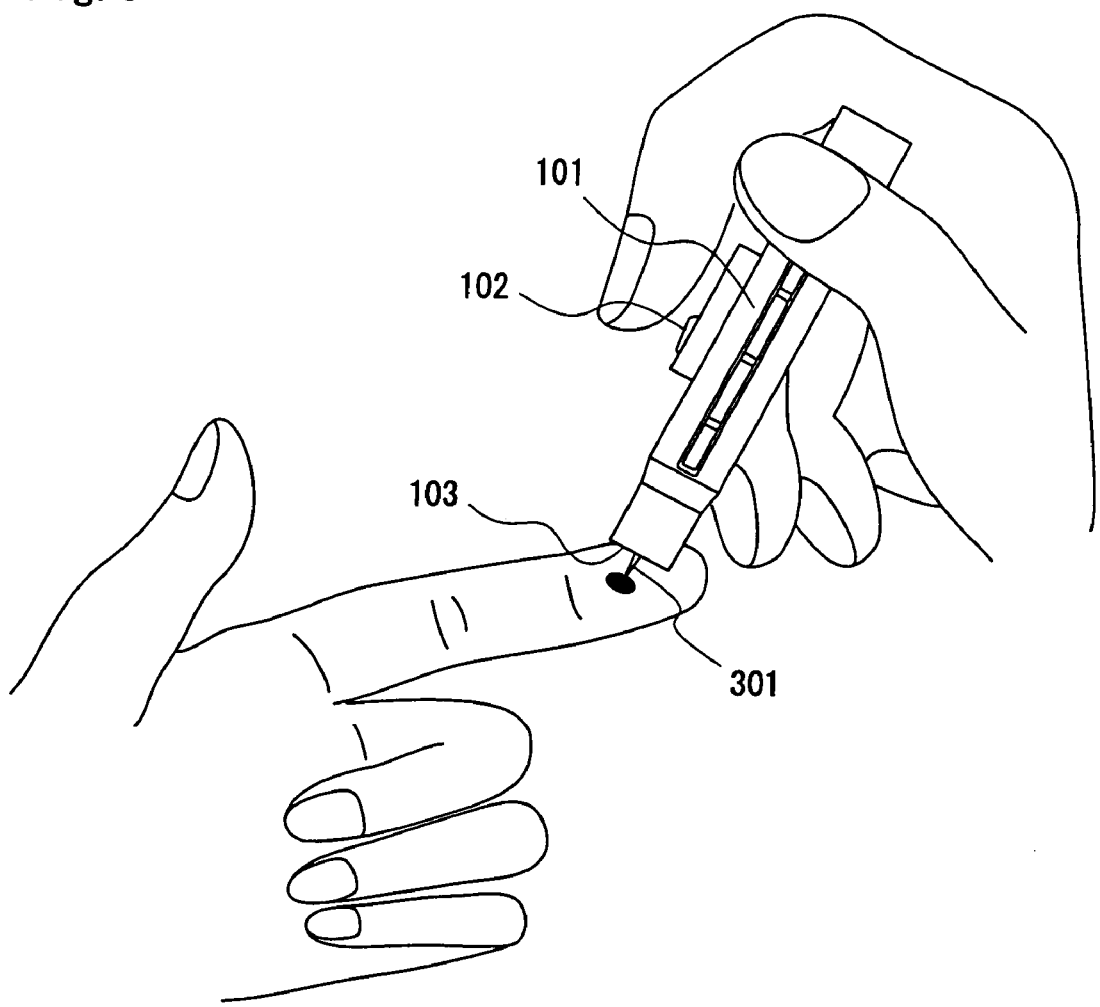
FIG. 8 is a diagram illustrating a puncture operation of the puncture instrument according to the first embodiment of the present invention.

By repeating the above-mentioned operation, the puncture operation to be performed when measuring blood sugar or the like can be carried out continuously, and the operator presses the puncture button 102 after the predetermined operation of the puncture needle replacement jig 107, whereby the operator can perform the puncture operation while lightly pressing the puncture portion such as finger tip or arm against the puncture portion pressing plane 103 as shown in FIG. 8, thereby to perform a series of blood collecting operations.

As described above, the puncture instrument set 100 according to the first embodiment is provided with the puncture needle cartridge 200 for holding plural puncture needles 201 which are arranged in series, the puncture needle cartridge stopping part 402 for stopping the puncture needle cartridge 200 at a predetermined position in its axis direction, the biasing member 403 for biasing the puncture needle cartridge 200 in one direction, and the puncture needle replacement jig 107 for setting the puncture needle cartridge 200 at the puncture operation start position and, simultaneously, removing the used puncture needle 201 after puncturing by the puncture needle. Therefore, the used puncture needle 201 is safely discarded and, simultaneously, a new puncture needle 201 is set at the puncture operation start position for a next puncture operation, by only inserting the puncture needle replacement jig 107 into the puncture instrument 101. Accordingly, it is possible to provide a high-safety puncture instrument which can continuously perform the puncture action by the simple construction.

Further, in this first embodiment, since the plural puncture needles 201 are arranged in series in the puncture needle cartridge 200, it is possible to provide a small-volume puncture instrument which can continuously perform the puncture operation.

In this first embodiment, in order to check the remaining quantity of the puncture needles 201 in the puncture needle cartridge 200, the remaining quantity check window 104 is provided on the side surface of the body 401 of the puncture instrument 101 as shown in FIG. 1 so that the remaining quantity of the puncture needles 201 can be easily checked from the outside until the plural puncture needles 201 in the puncture needle cartridge 200 are used up while sending the needles orderly. However, any method may be employed to check the remaining quantity of the puncture needles 201. For example, instead of providing the remaining quantity check window on the puncture instrument 101, the respective puncture needles 201 may be given serial numbers 307 by printing or carving as shown in FIG. 3(b). Alternatively, the respective puncture needles 201 may be colored, or the last puncture needle may be colored with red, thereby to check the remaining quantity of the puncture needles.

Embodiment 2

While in the first embodiment the puncture needle cartridge is embedded in the puncture instrument, in this second embodiment the puncture needle cartridge is detachably mounted on the puncture instrument.

Figure 9A:
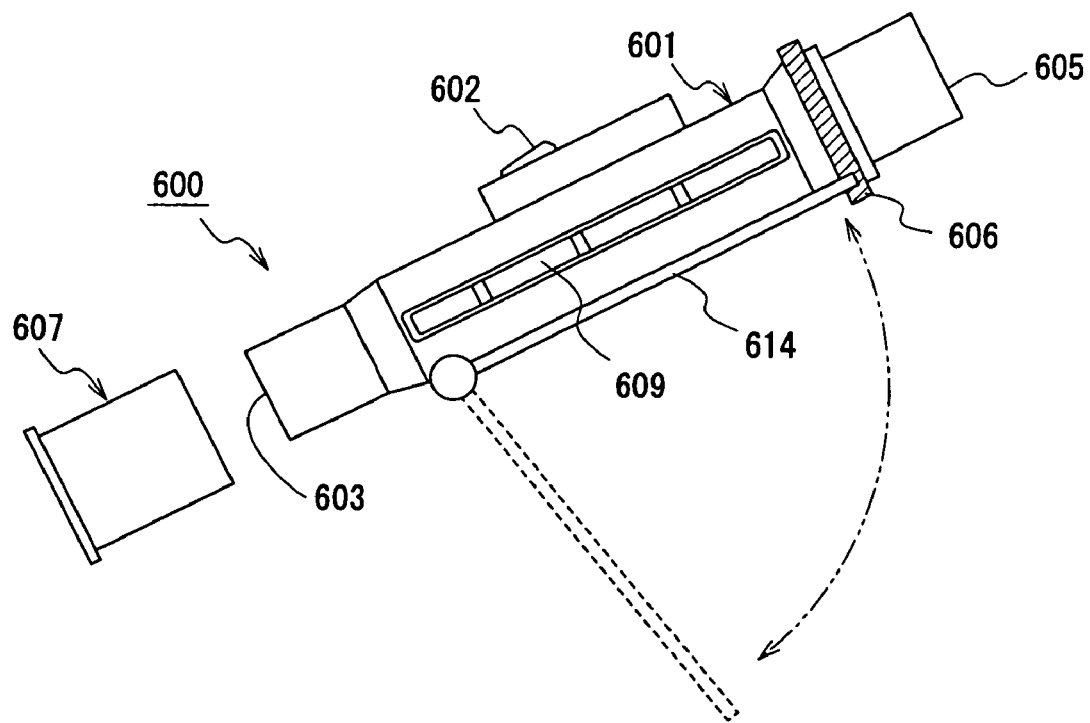
FIG. 9(a) is an outline view of a puncture instrument set according to a second embodiment of the present invention.

FIG. 9(a) is a diagram illustrating the construction of a puncture instrument set 600 according to the second embodiment.

In FIG. 9(a), the puncture instrument set 600 according to the second embodiment comprises, like the first embodiment, a puncture instrument 601 for performing puncture operation, and a puncture needle replacement jig 607 for removing a puncture needle that is held in the puncture instrument 601 and, simultaneously, setting a next new puncture needle at a puncture operation start position.

The puncture instrument 601 according to the second embodiment is provided with a loading lid 614 that opens a portion of the puncture instrument 601 when attaching or detaching the puncture needle cartridge. The other constituents are identical to those described for the first embodiment, and therefore, repeated description is not necessary.

Hereinafter, the operation of attaching the puncture needle cartridge into the puncture instrument will be described with reference to FIG. 9(b).

Figure 9B:
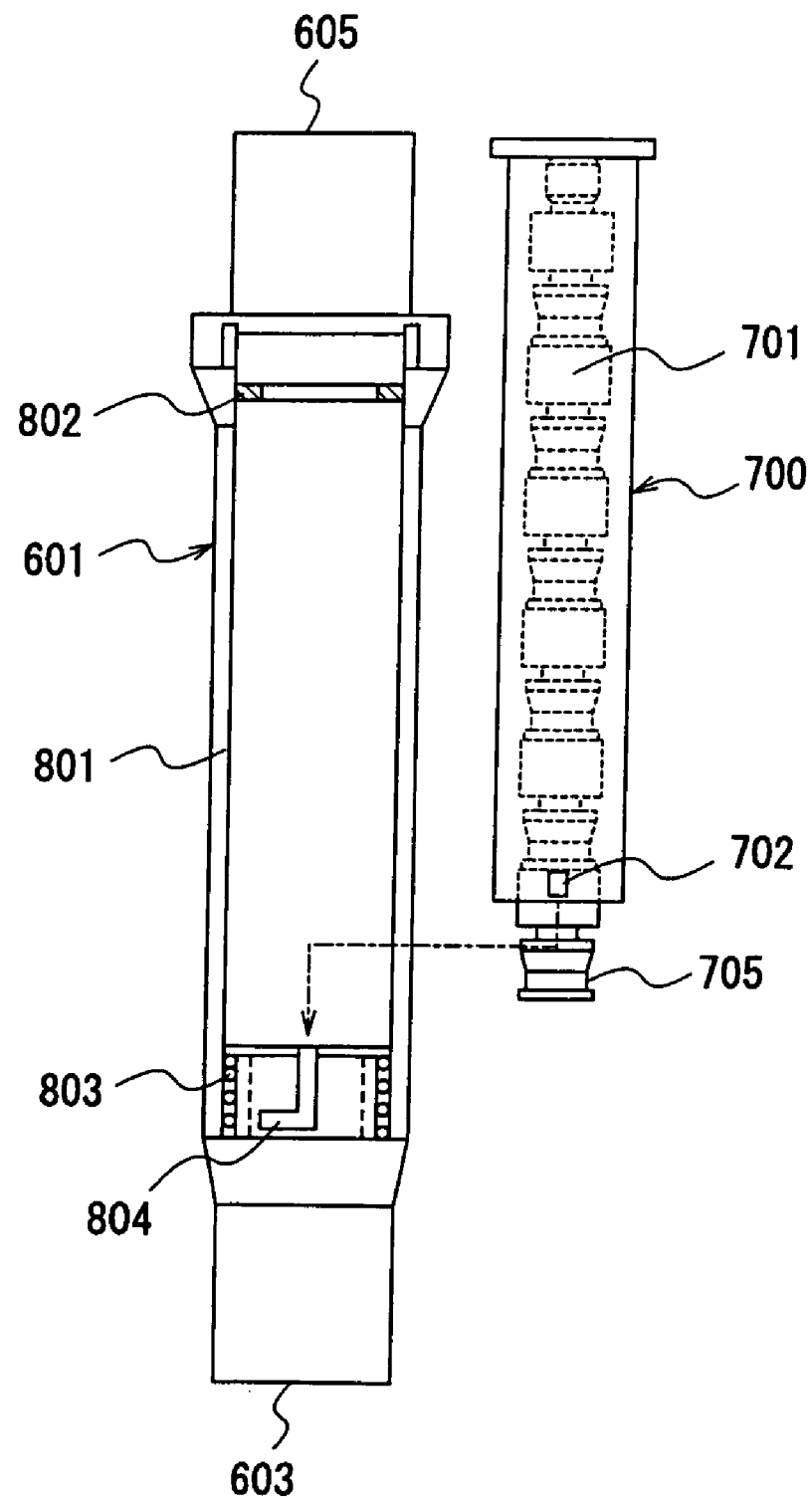
FIG. 9(b) is a diagram for explaining an operation of loading a puncture needle cartridge in a puncture instrument according to the second embodiment of the present invention.

FIG. 9(b) is a diagram for explaining the operation of attaching the puncture needle cartridge into the puncture instrument according to the second embodiment.

With reference to FIG. 9(b), there are provided, in a body 801 of the puncture instrument 601, a junction protrusion guide slit 804 for detachably holding the puncture needle cartridge 700 in the puncture instrument 601, in addition to a puncture needle cartridge stopper 802, a biasing member 803 comprising an elastic material, a set claw (not shown) which is one end of the puncture button 602, and a rotation stopper support (not shown).

The puncture needle cartridge 700 is provided with a junction protrusion 702 to be engaged with the protrusion guide slit 804 when the cartridge 700 is attached to the puncture instrument 601, and a cartridge stopper (not shown) for fixing the cartridge 700.

Next, the operation of the puncture instrument 601 according to the second embodiment will be described.

When attaching the puncture needle cartridge 700 into the puncture instrument 601, initially the loading lid 614 is opened to open the puncture instrument 601. In this state, the insertion direction of the puncture needle cartridge 700 is adjusted with respect to the puncture instrument 601, and the junction protrusion 702 is inserted up to the back of the junction protrusion guide slit 804 so that the junction protrusion 702 at the front end of the puncture needle cartridge 700 is fitted and fixed to the junction protrusion guide slit 804 at the front end of the puncture instrument 601, and thereafter, the puncture needle cartridge 700 is rotated around its axis up to a position where the rotation stops. This operation joins the puncture needle cartridge 700 and the puncture instrument 601. Thereafter, the loading lid 614 provided on the side surface of the body 801 of the puncture instrument 601 is closed to complete the operation of attaching the puncture needle cartridge 700 into the puncture instrument 601.

Thereafter, as in the first embodiment, among the puncture needles loaded into the puncture needle cartridge 700, a next new puncture needle 701 is orderly sent to the head of the puncture needle cartridge 700 simultaneously with removal of the puncture needle head cap 705, and furthermore, the puncture needle cartridge 700 is set at the puncture operation start position, by using the puncture needle replacement jig 607. Thereafter, as shown in FIG. 8, the user presses the puncture button 602 with the puncture portion such as finger tip or arm being lightly pressed against the puncture portion pressing plane 603, whereby puncturing is carried out to collect blood from the puncture portion of the user.

By repeating the above-mentioned operation, the puncture operation to be performed when measuring blood sugar or the like can be carried out continuously in the puncture instrument according to the second embodiment.

As described above, according to the puncture instrument 601 of the second embodiment, the puncture needle cartridge 700 integrated with the plural puncture needles is detachably mounted on the puncture instrument 701, whereby the puncture operation for blood collection can be carried out continuously and reliably, and furthermore, loading of the puncture needles can be carried out easily and reliably.

In this second embodiment, it is premised that the puncture needle cartridge in which plural puncture needles have previously been loaded is attached into the puncture instrument 601, and therefore, the operation of loading the puncture needle group into the puncture needle cartridge 700 is not specially described. However, as described for the first embodiment, the user may load plural puncture needles connected to each other as shown in FIG. 3(b) into the puncture needle cartridge 700, and thereafter, attach the puncture needle cartridge in which the puncture needles are loaded into the puncture instrument 601.

Embodiment 3

While in the first and second embodiments the puncture instrument set comprises the puncture instrument and the puncture needle replacement jig, in this third embodiment a description will be given of a case where a puncture instrument set comprises a puncture instrument, and a puncture needle disposal instrument which can remove used puncture needles from the puncture instrument and, further, safely store the used puncture needles to be discarded. In this third embodiment, it is assumed that the puncture instrument is one having the conventional construction in which a puncture needle is changed at each puncture operation.

Figure 10:
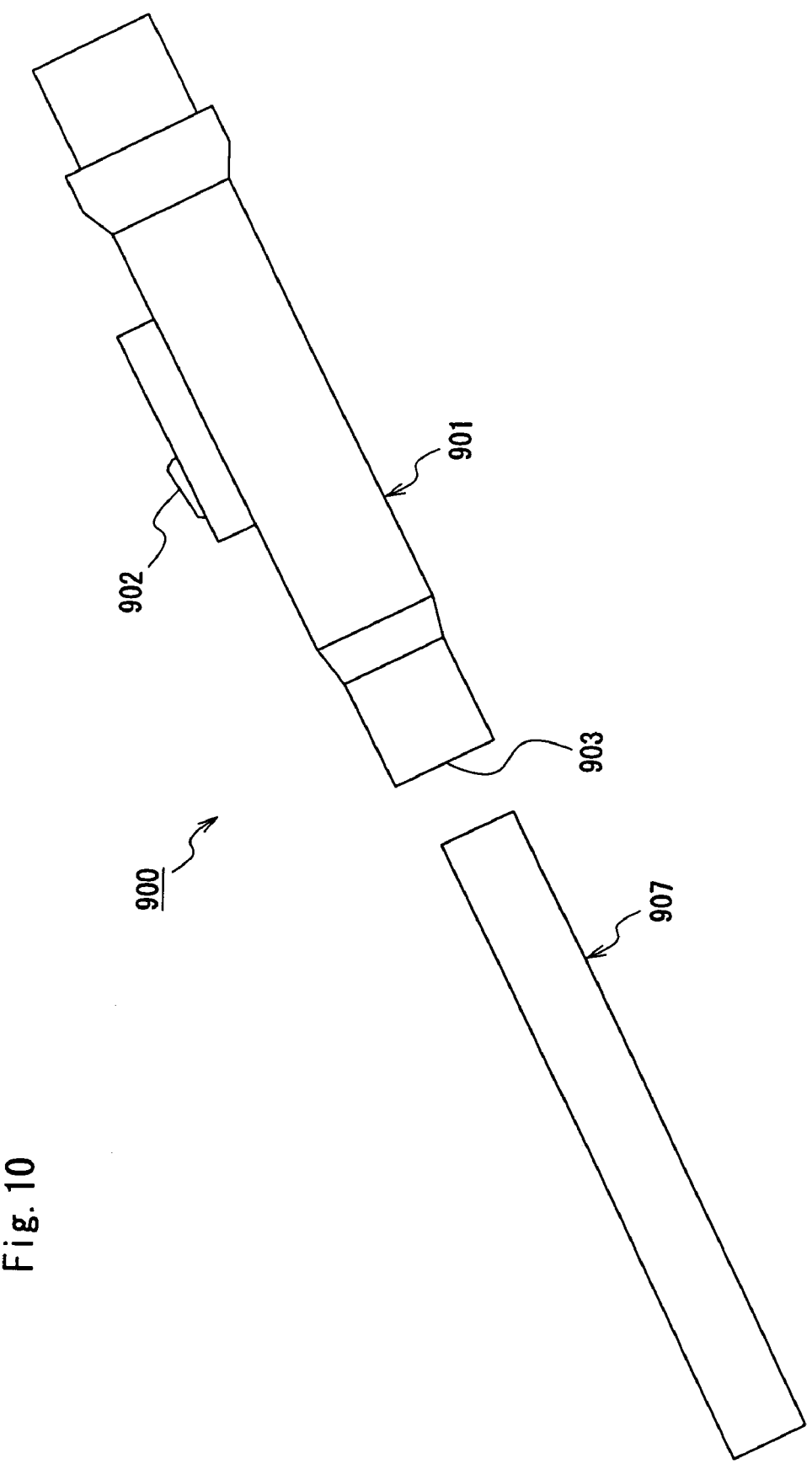
FIG. 10 is an outline view of a puncture instrument set according to a third embodiment of the present invention.

FIG. 10 is an external view of the puncture instrument set according to the third embodiment of the invention.

With reference to FIG. 10, the puncture instrument set 900 according to the third embodiment is provided with a puncture instrument 901 for performing puncture, and a puncture needle disposal instrument 907. The puncture needle disposal instrument 907 removes a used puncture needle from the puncture instrument 901 and stores the needle, and simultaneously, sets a next new puncture needle at a puncture operation start position.

The puncture instrument 901 is provided with a puncture button 902 for starting puncture operation, and a puncture portion pressing plane 903 to be applied to a puncture target portion (hereinafter referred to as "puncture portion") such as a finger of the user, and one puncture needle is detachably loaded in the puncture instrument 901.

Hereinafter, the third embodiment will be described in detail with reference to FIGS. 11 to 13.

Figure 11A:
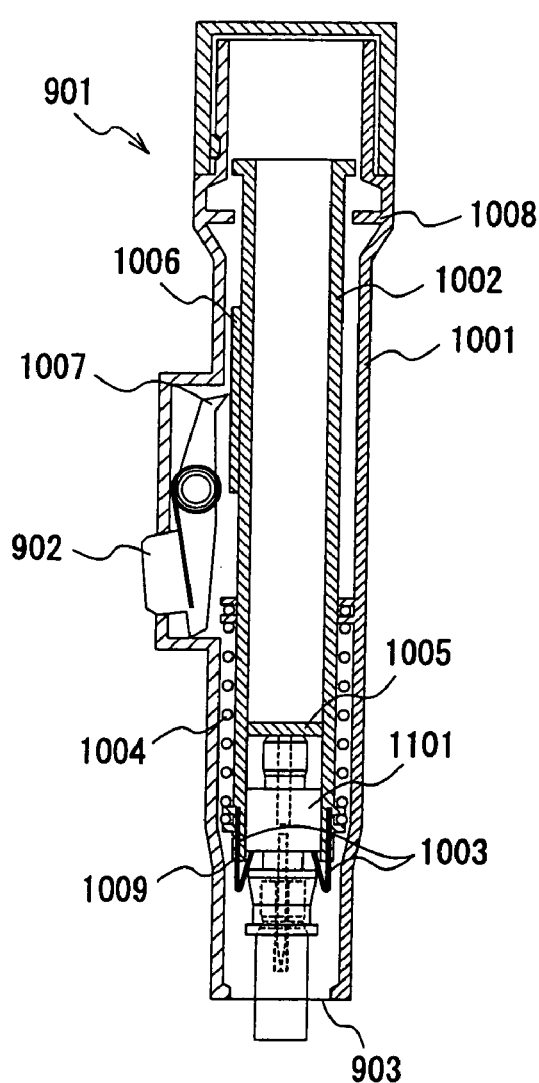
FIG. 11(a) is a cross-sectional view of a puncture instrument according to the third embodiment of the present invention.

FIG. 11(a) is a cross-sectional view of the puncture instrument in which a puncture needle is loaded, according to the third embodiment.

In the figure, there are provided, in a body 1001 of the puncture instrument 901, a slider 1002, a puncture needle retaining elastic member 1003, a biasing member 1004, a puncture needle stopper 1005, a set claw engagement part 1006, a set claw 1007, and a slider stopper 1008.

The slider 1002 is embedded in the body 1001 of the puncture instrument 901, a puncture needle 1101 is attached to a front end of the slider 1002, and the slider 1002 moves in the body 1001 in its axis direction. The puncture needle retaining elastic member 1003 is an elastic member such as a plate spring disposed at the front end of the slider 1002, and the puncture needle 1101 is detachable with respect to the elastic member 1003. The elastic member 1003 prevents the puncture needle 1101 from dropping off of the slider 1002.

The biasing member 1004 biases the slider 1002 toward the puncture portion pressing plane 903 that is the front end of the puncture instrument 901, and a compression spring is employed as an example of the biasing member in this third embodiment. The puncture needle stopper 1005 stops the puncture needle 1101 at a predetermined position in the slider 1002. The set claw 1007 is disposed at an end of the puncture button 902, and is engaged with the set claw engagement part 1006 to maintain the slider 1002 at the puncture operation start position. The slider stopper 1008 is integrated with the body 1001, and stops the slider 1002 at a predetermined position in the body 1001. Reference numeral 1009 denotes a front end surface of the slider 1002, which contacts a cylinder end surface 1202 of the puncture needle disposal instrument 907 to be described later.

Figure 12:
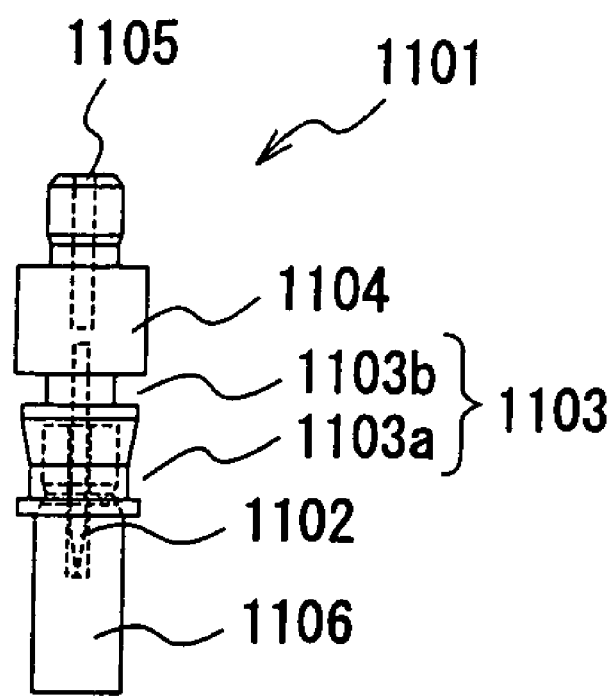
FIG. 12 is a diagram illustrating the construction of a puncture needle according to the third embodiment of the present invention.

FIG. 12 is a diagram illustrating the construction of the puncture needle according to the third embodiment. As shown in the figure, the puncture needle 1101 according to the third embodiment comprises a needle portion 1102, and an elastic deformation part 1104 formed by means such as injection molding, which are integrated with each other. A rear end portion of the puncture needle 1101 has a shape to be fitted to a front end portion of a next puncture needle so that the used disposal puncture needles 1101' are fitted to each other in the puncture needle disposal instrument 907 to be described later. Further, the rear end portion of the puncture needle 1101 has a hole 1101 into which the needle portion 1102 of the next puncture needle is inserted. The elastic deformation part 1104 of each puncture needle 1101 has dents 1103a and 1103b, and the puncture needle 1101 can be held by the slider 1102 when the puncture needle stopping member 1003 of the slider 1002 engages into the dent 1103b, and further, replacement and disposal of the used puncture needle 1101' can be carried out when a disposal instrument return member of the puncture needle disposal instrument 907 to be described later engages into the dent 1103a.

Moreover, the needle portion 1102 of each puncture needle 1101 is provided with a protection cover 1106 so as to prevent the user form being injured during the operation of attaching the puncture needle 1101.

The puncture needle 1101 having the above-mentioned construction is loaded into the slider 1002 of the puncture instrument 901, with the protection cover 1106 being attached to the front end thereof, as shown in FIG. 11(a).

Figure 11B:
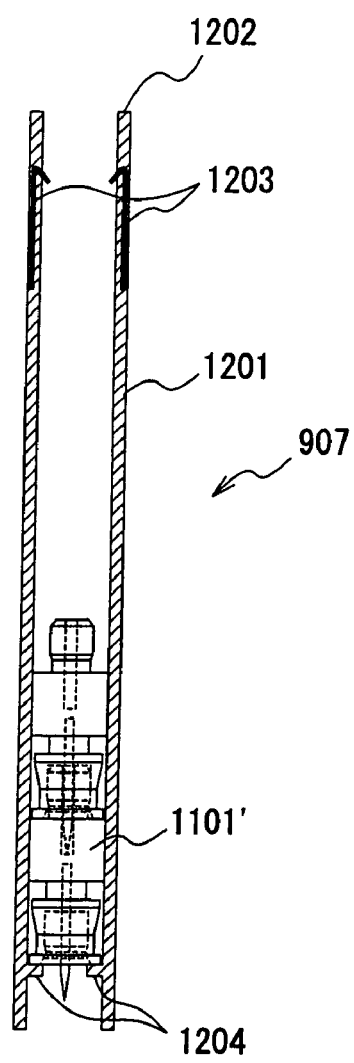
FIG. 11(b) is a cross-sectional view of a puncture needle disposal instrument according to the third embodiment of the present invention.

On the other hand, FIG. 11(b) is a diagram illustrating a cross-section of the puncture needle disposal instrument according to the third embodiment of the present invention. In the figure, the puncture needle disposal instrument 907 according to the third embodiment is provided with a cylindrical part 1201, a disposal instrument pressing part 1202, a disposal puncture needle stopping part 1204, and a disposal instrument return member 1203.

The cylindrical part 1201 has a cylindrical configuration, and the used disposal puncture needle 1101' can be inserted and stored therein. The disposal puncture needle stopping unit 1204 prevents the disposal puncture needle 1101' from dropping out of the cylindrical part 1201, and the disposal instrument pressing part 1202 dissolves holding of the puncture needle 1101 by the puncture needle retaining elastic member 1003 of the slider 1002. The disposal instrument return member 1203 engages into the dent 1103a of the puncture needle 1101 as shown in FIG. 13 to hold the puncture needle 1101 one by one.

Hereinafter, the puncture operation of the puncture instrument according to the third embodiment of the present invention will be described with reference to FIG. 13.

Figure 13A:
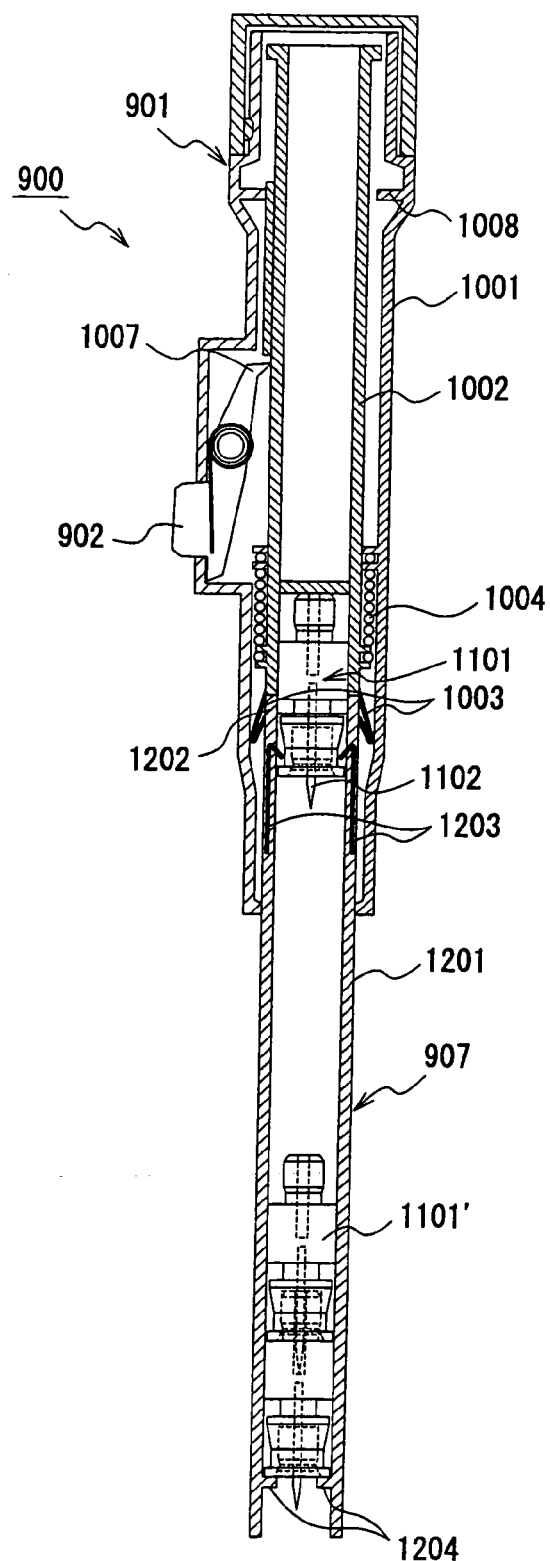
FIG. 13(a) is a diagram for explaining an operation of discarding a used puncture needle in the puncture instrument set according to the third embodiment of the present invention.
Figure 13B:
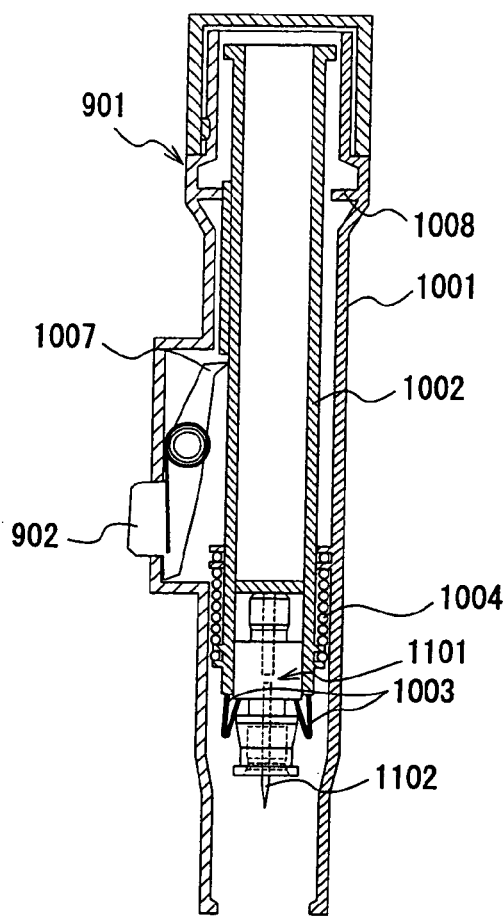
FIG. 13(b) is a diagram illustrating the puncture instrument in a state where a new puncture needle is loaded, according to the third embodiment of the present invention.

FIG. 13(a) is a diagram for explaining the operation of discarding a used puncture needle from the puncture instrument according to the third embodiment, and FIG. 13(b) is a diagram illustrating the puncture instrument loaded with a new puncture needle according to the third embodiment.

Initially, in order to remove and discard the used disposal puncture needle 1101' from the puncture instrument 901 in the state shown in FIG. 11(a), the puncture needle disposal instrument 907 is inserted from the puncture portion pressing plane 903 of the puncture instrument 901. Thereby, as shown in FIG. 13(a), the puncture needle retaining elastic member 1003 of the puncture instrument 901 is pushed by the end surface 1202 of the cylindrical part 1201 to dissolve the state where the puncture needle retaining elastic member 1003 engages into the dent 1103b of the puncture needle 1101.

When the puncture needle disposal instrument 907 is further inserted from the puncture portion pressing plane 903 of the puncture instrument 901, the disposal instrument return member 1203 of the puncture needle disposal instrument 907 elastically bends and thereafter engages into the dent groove 1103a of the puncture needle 1101. Thereby, the used disposal puncture needle 1101' is held by the puncture needle disposal instrument 907.

Thereafter, when the puncture needle disposal instrument 907 is further inserted, the disposal instrument pressing part 1202 pushes up the puncture needle retaining elastic member 1003 of the slider 1002 while withstanding the return force of the biasing member 1004 of the puncture instrument 901, and moves the whole slider 1002 to the rear end side of the body 1001 of the puncture instrument 901. Finally, as shown in FIG. 13, the puncture needle disposal instrument 907 is pushed into the puncture instrument 901 to push up the slider 1002 until the set claw engagement part 1006 disposed at the surface of the slider 1002 is engaged with the set claw 1007 disposed at an end of the puncture button 902 of the puncture instrument 901.

When the set claw engagement part 1006 is stopped by the set claw 1007, the slider 1002 in the puncture instrument 901 does not return to the initial position (FIG. 11) again due to the recovery force of the biasing member 1004, thereby the slider 1002 can be set to the puncture start position.

The puncture instrument 901 is pulled out of the puncture needle disposal instrument 907 from this state, whereby the used puncture needle 1101' which has been held by the disposal instrument return member 1203 is removed from the slider 1002 of the puncture instrument 901 together with the puncture needle disposal instrument 907. Thereafter, the removed disposal puncture needle 1101' is pushed into the cylindrical part 1201 with a light force, and falls down until it contacts the disposal puncture needle stopping part 1204 at the bottom of the puncture needle disposal instrument 907. As a result, the disposal puncture needle 1101' can be easily and safely removed and discarded.

Of course, the puncture needle disposal instrument 907 can store plural pieces of disposal puncture needles 1101' in it. Further, as shown in FIG. 13, when there already exists a disposal puncture needle 1101' in the puncture needle disposal instrument 907, the front end of the removed disposal puncture needle 1101' is fitted to the rear end of the disposal puncture needle 1101' stored in the puncture needle disposal instrument 907, and the needle portion 1102 of the removed puncture needle 1101' is inserted into the hole 1104 at the rear end of the disposal puncture needle 1101' stored in the disposal instrument, whereby the volume of the disposal puncture needles 1101' in the cylindrical part 1201 of the puncture needle disposal instruction 907 is reduced.

On the other hand, although load is applied to the slider 1002 when the used disposal puncture needle 1101' is removed from the slider 1002 of the puncture instrument 901 by the puncture needle disposal instrument 907 as described above, since the set claw 1007 stops the set claw engagement part 1006, the slider 1002 does not move from the puncture operation start position.

Accordingly, when a next new puncture needle is loaded into the slider 1002 of the puncture instrument 901, the new puncture needle 1101 is pushed up to the puncture needle retaining elastic member 1003 of the puncture instrument 901 and fixed, with the protection cover 1106 being attached to the new puncture needle 1101, and thereafter, the protection cover 1106 is removed, thereby setting the puncture instrument in the puncture ready state. Thereafter, as shown in FIG. 8, the user presses the puncture button 902 with the puncture portion such as finger tip or arm being lightly pressed against the puncture portion pressing plane 903, whereby the user can perform puncturing to perform a series of blood collecting operations.

When the disposal puncture needles 1101' are piled up in the cylindrical part 1201 of the puncture needle disposal instrument 907 by repeating the above-mentioned operation, the puncture needles 1101' are discarded together with the puncture needle disposal instrument 907, or the puncture needle disposal instrument 907 is brought to a predetermined place to discard only the disposal puncture needles 1101'.

As described above, the puncture needle disposal instrument 907 according to the third embodiment comprises the cylindrical part 1201 which dissolves engagement between the used disposal puncture needle 1101' and the puncture needle retaining elastic member 1003 and is able to store the disposal puncture needles 1101' removed from the puncture instrument; the disposal puncture needle stopping part 1204 for preventing the disposal puncture needle 1101' from dropping out of the cylindrical part 1201; the disposal instrument pressing part 1202 for dissolving engagement between the puncture needle retaining elastic member 1003 of the puncture instrument 901 and the puncture needle 1101; and the disposal instrument return member 1203 which engages into the dent 1103a of the puncture needle 1101 to hold the puncture needles 1101 one by one. Therefore, the disposal puncture needle 1101' after use can be safely removed by simple operation.

Further, since the puncture needle disposal instrument 907 is provided with the cylindrical part, plural pieces of disposal puncture needles 1101' after use, which are removed from the puncture instrument, can be stored in the cylindrical part, thereby reducing the effort in the subsequent disposal processing.

While in this third embodiment the puncture instrument of the conventional construction in which a puncture needle is set in the slider 1002 every time puncturing is carried out is described as an example, the third embodiment may employ the puncture instrument including the puncture needle cartridge that can hold plural puncture needles, as described for the first and second embodiment. In this case, a next new puncture needle stored in the puncture needle cartridge is sent forward simultaneously with removal of the disposal puncture needle 1101' after use by the puncture needle disposal instrument 907, thereby saving the trouble of setting a new puncture needle in the puncture instrument every time puncturing is ended, resulting in more safe and simple puncture operation.

The whole or part of the cylindrical part 1201 of the puncture needle disposal instrument 907 may be composed of a transparent material. In this case, it becomes easy to check the attachment/detachment state and the storage state of the used disposal puncture needles 1101'.

Embodiment 4

In the above-mentioned third embodiment, the puncture needle disposal instrument for discarding puncture needles is provided with the cylindrical part having a cylindrical configuration, and the disposal puncture needles are stored in the cylindrical part. On the other hand, a puncture needle disposal instrument according to this fourth embodiment is provided with a cylindrical part, and a disposal box for storing disposal puncture needles, into which the cylindrical part can be inserted. In this fourth embodiment, a description will be given of the case where a new puncture needle is set in the puncture instrument every time a puncture operation is ended, as in the conventional construction.

Figure 14:
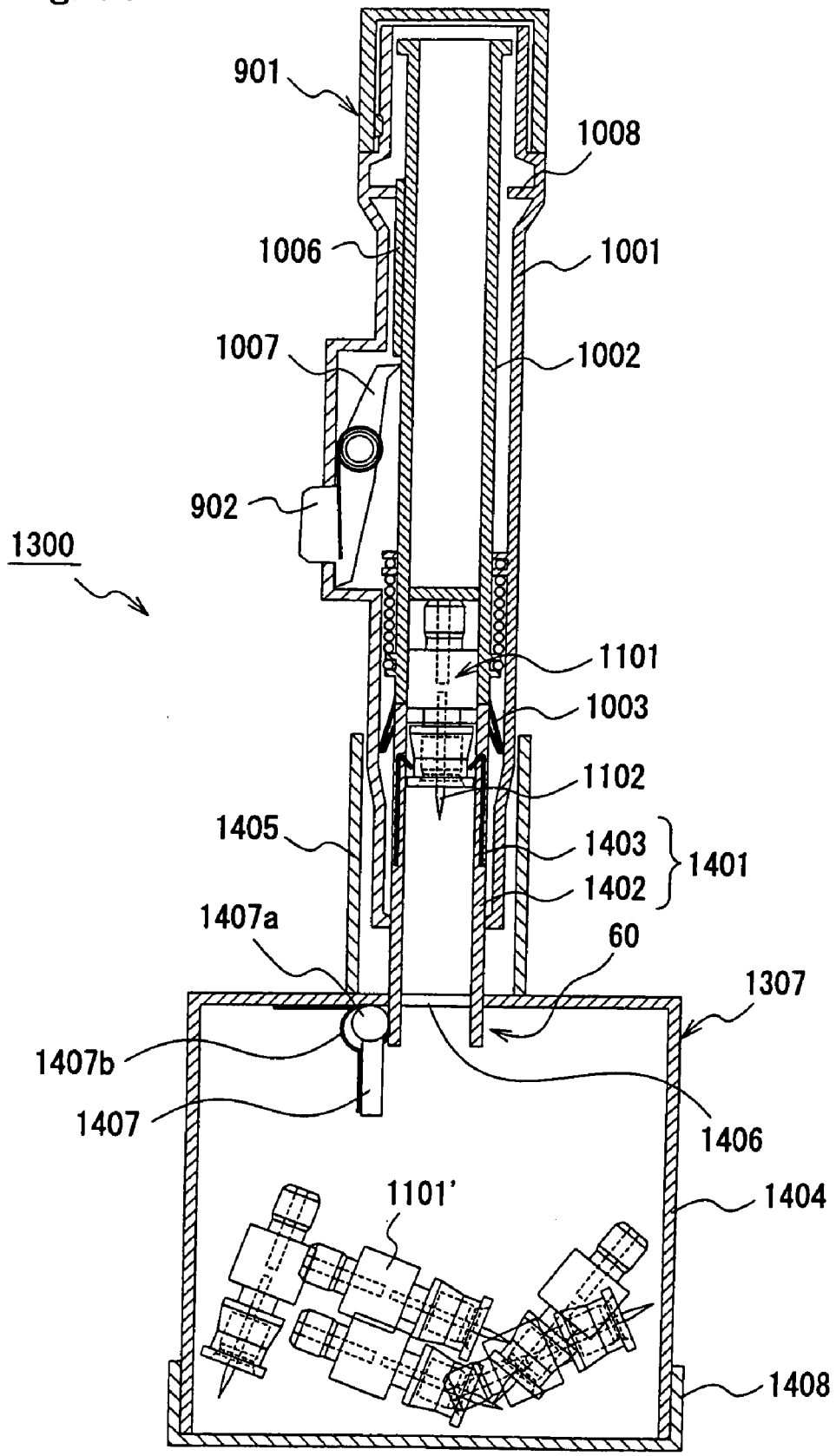
FIG. 14 is a diagram for explaining an operation of discarding a used puncture needle, in a puncture instrument set according to a fourth embodiment of the present invention.

FIG. 14 is a diagram illustrating the cross-section of a puncture instrument set according to the fourth embodiment.

In FIG. 14, the puncture instrument set 1300 according to the fourth embodiment comprises a puncture instrument 901, and a puncture needle disposal instrument 1307 which takes a used disposal puncture needle 1101' out of the puncture instrument 901 and stores it, and simultaneously, sets a next new puncture needle in a puncture operation start position.

The puncture needle disposal instrument 1307 according to the fourth embodiment comprises a cylindrical part 1401, and a disposal box 1405 in which disposal puncture needles 1101' are stored. The puncture needle disposal instrument 1307 is separable into the cylindrical part 1401 and the disposal box 1404, and fitting between the cylindrical part 1401 and the disposal box 1404 is detachably realized by connecting the disposal box 1404 and the cylindrical part 1401 using light press fitting or screws.

The cylindrical part 1401 is provided with a disposal instrument pressing part 1402 which dissolves holding of the puncture needle 1101 by the puncture needle retaining elastic member 1003 of the slider 1002, and a disposal instrument return member 1403 which engages into the dent 1103a of the puncture needle 1101 loaded in the slider 1002 of the puncture instrument 901 as shown in FIG. 14 so as to hold the puncture needle 1101 one by one.

On the other hand, a part or the whole of the disposal box 1404 is formed of a transparent material, and an external cylindrical part 1405 for guiding the outer shape of the body 1001 of the puncture instrument 901 and an opening part 1406 that is opened by an open/close lid 1407 are provided at the upper surface of the disposal box 1404. The opening part 1406 is fitted to the cylindrical part 1401 so as to be continuous with the cylindrical part 1401. The open/close lid 1407 is supported rotatably on a supporting point 1407a thereof, and the lid 1407 is biased counterclockwise by an open/close spring 1407b. Therefore, when the cylindrical part 1401 is separated from the disposal box 1405, the open/close lid 1407 that has been biased by the open/close spring 1407b is closed. Further, a disposal cap 1408 is detachably provided at the lower surface of the disposal box 1405.

Hereinafter, the puncture operation of the puncture instrument according to the fourth embodiment of the present invention will be described with reference to FIG. 14.

As described for the third embodiment, initially, in order to remove the used disposal puncture needle 1101' from the puncture instrument 901, the cylindrical part 1404 of the puncture needle disposal instrument 1307 is inserted from the puncture portion pressing plane 903 of the puncture instrument 901. Thereby, as shown in FIG. 14, the puncture needle retaining elastic member 1003 of the puncture instrument 901 is pushed by the end surface of the inner cylindrical part 1402 of the cylindrical part 1401 to dissolve engagement of the puncture needle retaining elastic member 1003 into the dent 1103b of the puncture needle 1101. Then, the cylindrical part 1401 of the puncture needle disposal instrument 1307 is further inserted from the puncture portion pressing plane 903 of the puncture instrument 901, whereby the disposal instrument return member 1403 of the cylindrical part 1401 elastically bends and thereafter engages into the dent groove 1103a of the puncture needle 1101'. Thereby, the used disposal puncture needle 1101' is held by the cylindrical part 1401 of the puncture needle disposal instrument 1307.

Thereafter, when the puncture needle disposal instrument 1307 is further inserted, the disposal instrument pressing part 1402 pushes up the puncture needle retaining elastic member 1003 of the slider 1002 while withstanding the return force of the biasing member 1004 of the puncture instrument 901, and moves the whole slider 1002 to the rear end side of the body 1001 of the puncture instrument 901. Then, the puncture needle disposal instrument 907 is pushed into the puncture instrument 901 until the set claw 1007 disposed at an end of the puncture button 902 of the puncture instrument 901 is engaged with the set claw engagement part 1006 disposed at the surface of the slider 1002. Thereby, the slider 1002 in the puncture instrument 901 can be set at the puncture start position, without permitting the slider 1002 to return to the initial position due to the recovery force of the biasing member 1004.

In this state, the front end of the cylindrical part 1401 of the puncture needle disposal instrument 1307 is inserted in the opening part 1406 along the outer cylindrical part 1405 of the disposal box 1404, as shown in FIG. 14.

Thereafter, the puncture instrument 901 is moved upward, whereby the disposal puncture needle 1101' after use is separated from the puncture instrument 901 and pulled out toward the cylindrical part 1401, and the used disposal puncture needle 1101' pulled out to the cylindrical part side drops into the disposal box 1404 to be discarded.

On the other hand, although load is applied to the slider 1002 when the used disposal puncture needle 1101' is removed from the slider 1002 of the puncture instrument 901 by the puncture needle disposal instrument 1307 as described above, since the set claw 1007 latches the set claw engagement part 1006, the slider 1002 does not move from the puncture operation start position.

Accordingly, when a next new puncture needle is loaded in the slider 1002 of the puncture instrument 901, the new puncture needle 1101 with the protection cover 1106 being attached thereto is pushed up to the puncture needle retaining elastic member 1003 of the puncture instrument 901 and fixed, and thereafter, the protection cover 1106 is removed, thereby setting the puncture instrument 901 in the puncture ready state.

Thereafter, as shown in FIG. 8, the user presses the puncture button 902 with the puncture portion such as finger tip or arm being lightly pressed against the puncture portion pressing plane 903, whereby the user can perform puncturing to perform a series of blood collecting operations.

When the disposal puncture needles 1101' are piled up in the disposal box 1401 of the puncture needle disposal instrument 1307 by repeating the above-mentioned operation, the disposal puncture needles 1101' stored in the disposal box 1404 are discarded.

At this time, since the puncture needle disposal instrument 1307 according to the fourth embodiment is separable into the cylindrical part 1401 and the disposal box 1404, only the disposal box 1404 in which the disposal puncture needles 1101' are stored may be discarded. Alternatively, the whole puncture needle disposal instrument 1307, which is not separated, may be discarded. When the cylindrical part 1401 and the disposal box 1404 are separated from each other, the opening part 1406 connecting the cylindrical part 1401 and the disposal box 1404 is closed by the open/close lid 1407, whereby the disposal puncture needles 1101' after use which are stored in the disposal box 1404 are prevented from getting out of the disposal box 1404 by accident.

Further, the disposal puncture needles 1101' can be discarded in another place by using the separable disposal cap 1408 that is provided at the lower surface of the disposal box 1404.

As described above, the puncture needle disposal instrument 1307 according to the fourth embodiment is provided with the cylindrical part 1401 for dissolving engagement between the used disposal puncture needle 1101' and the puncture needle retaining elastic member 1003, and the disposal box 1404 for storing the disposal puncture needles 1101' removed from the puncture instrument 901. Therefore, the disposal puncture needle 1101' is safely detached by simple operation, and further, the detached disposal puncture needle 1101' is dropped and stored in the disposal box 1404, thereby reducing the effort in the subsequent disposal processing.

Further, in the puncture needle disposal instrument 1307, when the cylindrical part 1401 and the disposal box 1404 are separated from each other, the opening part 1406 connecting the cylindrical part 1401 and the disposal box 1404 is closed by the open/close lid 1407. Therefore, even if the cylindrical part 1401 and the disposal box 1404 are separated from each other when discarding the disposal puncture needles 1101', the used disposal puncture needles 1101' stored in the disposal box 1404 are prevented from getting out of the disposal box by accident.

Further, since the puncture needle disposal instrument 1307 is provided with the outer cylindrical part 1405, the puncture instrument 901 to which the cylindrical part 1401 of the puncture needle disposal instrument 1307 is attached can be guided to the opening part 1406 of the disposal box 1404 with higher accuracy, thereby enhancing the controllability.

While in this fourth embodiment the puncture instrument is constructed such that the puncture needle is replaced every time the puncture operation is finished, this fourth embodiment is also applicable to the case where the puncture instrument includes the puncture needle cartridge as described for the third embodiment.

Embodiment 5

In a fifth embodiment, an outer cylindrical part of a puncture needle disposal instrument is provided with a stopper, thereby enhancing reliability of breakage prevention and control of the puncture needle disposal instrument.

Figure 15:
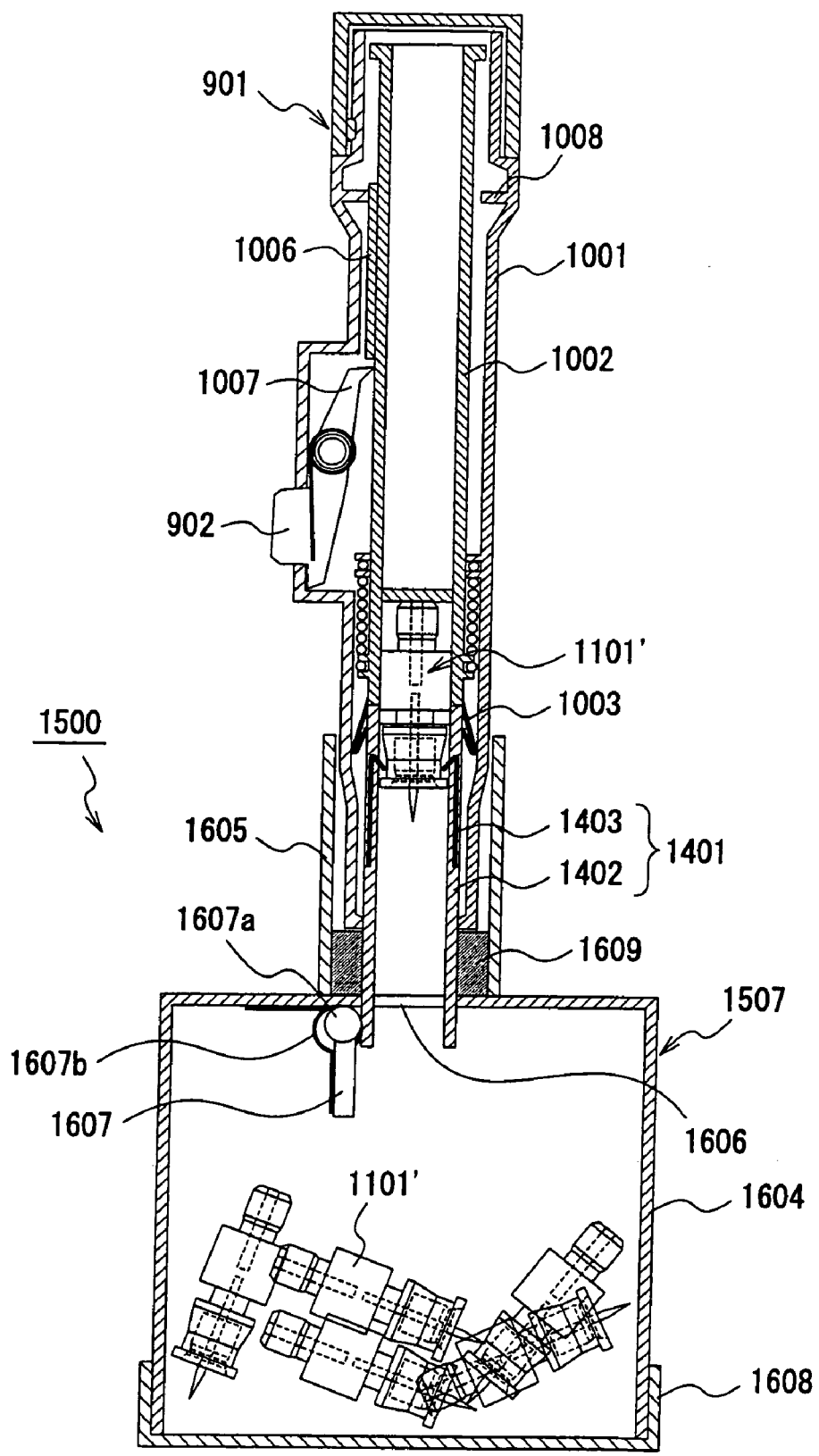
FIG. 15 is a diagram for explaining an operation of discarding a used puncture needle, in a puncture instrument set according to a fifth embodiment of the present invention.
Figure 16:
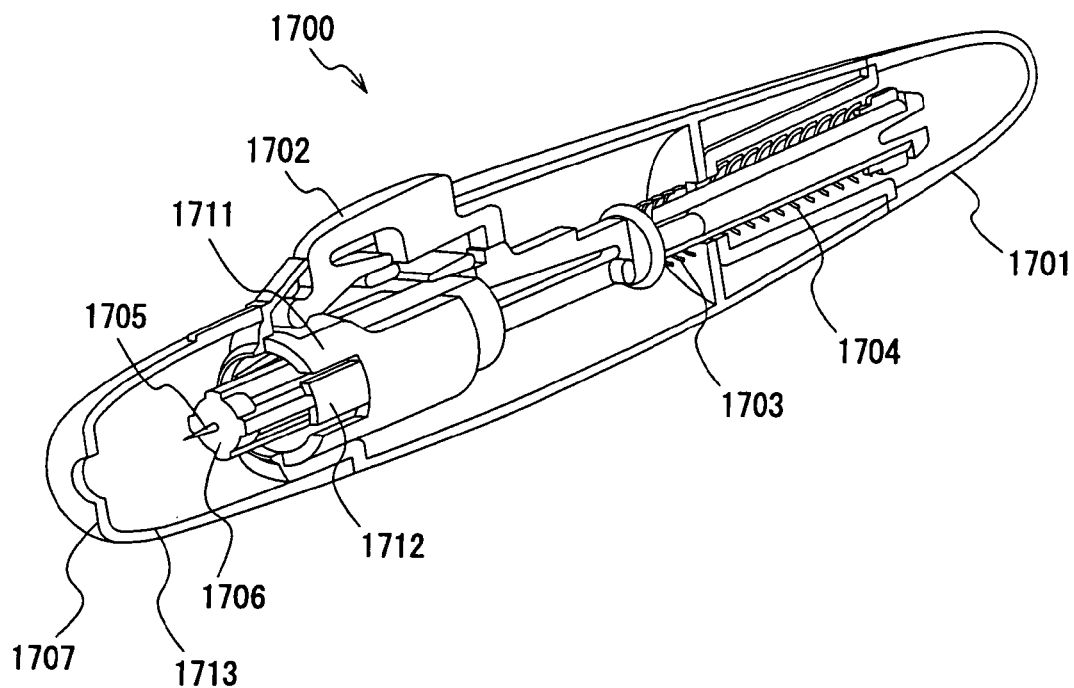
FIG. 16 is an outline view of a conventional puncture instrument.
Figure 17A:
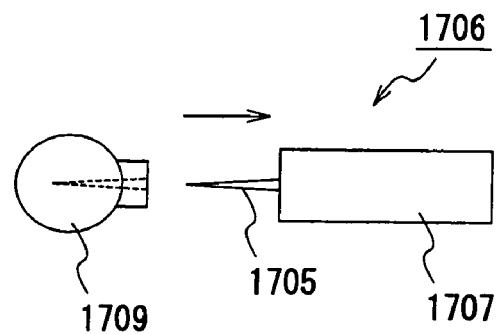
FIG. 17(a) is a diagram illustrating a puncture needle to be attached to the conventional puncture instrument, and a plastic cover of the puncture needle.
Figure 17B:
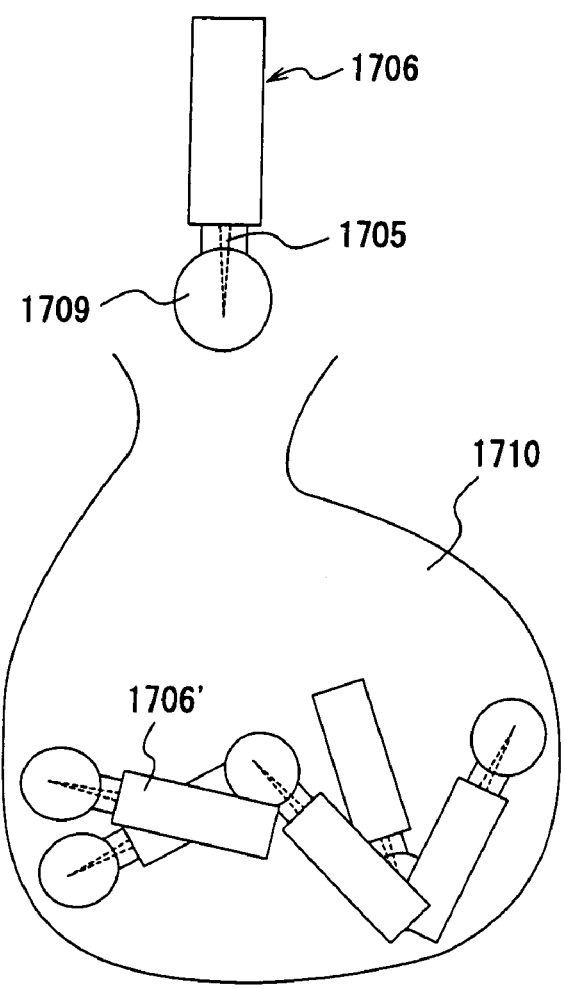
FIG. 17(b) is a diagram illustrating a conventional puncture needle disposal method.

FIG. 15 is a diagram illustrating the cross-section of the puncture instrument set according to the fifth embodiment.

In the figure, the puncture instrument set 1500 according to the fifth embodiment comprises a puncture instrument 901 for performing puncture operation, and a puncture needle disposal instrument 1507 for removing a disposal puncture needle 1101' that has been used from the puncture instrument 901 and storing the disposal puncture needle, and simultaneously, setting a next new puncture needle at a puncture operation start position.

Although the construction of this fifth embodiment is almost the same as that of the fourth embodiment, a stopper 1609 for stopping the puncture instrument 901 when the puncture instrument 901 equipped with the cylindrical part 1401 is pushed into the disposal box 1604 is disposed between the disposal box 1604 or the cylindrical part 1401, and the outer cylindrical part 1605. Since the other constituents are identical to those described for the fourth embodiment, repeated description is not necessary.

Hereinafter, the puncture operation of the puncture instrument according to the fifth embodiment of the present invention will be described with reference to FIG. 15.

Initially, in order to remove a used disposal puncture needle 1101' from the puncture instrument 901, the cylindrical part 1401 of the puncture needle disposal instrument 1507 is inserted from the puncture portion pressing plane 903 of the puncture instrument 901. Then, the puncture instrument 901 to which the cylindrical part 1401 of the puncture needle disposal instrument 1507 is attached is pushed into the disposal instrument 1604, thereby performing disposal of the disposal puncture needle 1101' as well as setting of the slider 1002 at the puncture operation start position.

As described above, in this fifth embodiment, the stopper 1609 is provided between the disposal box 1604 or the cylindrical part 1401, and the outer cylindrical part 1605. Accordingly, when the puncture instrument 901 to which the cylindrical part 1401 of the puncture needle disposal instrument 1507 is attached is pushed into the disposal instrument 1604 to perform disposal of the disposal puncture needle 1101' and setting of the slider 1002 at the puncture operation start position, the front end of the cylindrical part 1401 cannot move beneath the stopper 1609. As a result, it is possible to avoid that the cylindrical part 1401 of the disposal instrument enters excessively into the opening part 1606 and thereby the opening part is broken, and that a large stress is applied to the cylindrical part 1401 and thereby the puncture needle retaining elastic member 1003 is broken, thereby improving breakage prevention of the puncture needle disposal instrument 1507 and certainty of control.

As described above, the puncture needle disposal instrument 1507 according to the fifth embodiment is provided with the stopper 1609 disposed between the disposal box 1604 or the cylindrical part 1401, and the outer cylindrical part 1605. Therefore, when the puncture instrument 901 to which the cylindrical part 1401 is attached is pushed into the opening part 1606 of the disposal box 1604, the stopper 1609 avoids that the front end of the cylindrical part 1401 enters excessively into the opening part 1606 and that a large stress is applied to the cylindrical part 1401 to break the puncture needle retaining elastic member 1003. Furthermore, certainty of control is improved.

In the above-mentioned third to fifth embodiments, not only the disposal box of the disposal instrument but also the cylindrical part may be formed of a transparent material. In this case, the attachment/detachment state and storage state of the used disposal puncture needles 1101' can be easily checked.

APPLICABILITY IN INDUSTRY

In a puncture instrument set according to the present invention, a puncture needle is safely removed from a puncture instrument by a simple operation, and further, the removed disposal puncture needle after use is stored in a disposal instrument. Therefore, a diabetic patient who is visually handicapped can safely and easily handle the puncture instrument, and the trouble of discarding the used puncture needle can be reduced.

The invention claimed is:

1. A puncture instrument comprising a plurality of puncture needles for puncturing the surface of a biologic body and for performing seriatim puncturing with each of the puncture needles, said puncture instrument comprising:
   a puncture needle cartridge for housing a plurality of puncture needles connected in series in an axis direction of the puncture instrument,
   each puncture needle comprising a body member and a needle member, wherein a base end of the needle member is secured in and substantially coaxial with the body member, and a needle point end protrudes forwardly; and the body member comprising a forward end and a rear end, wherein the forward end extends in the axial direction of the needle member to surround the needle point end, such that when connected to a second puncture needle, the forward end covers the outer surface of the rear end of the second puncture needle, and wherein the forward end and the rear end have substantially complementary shapes such that the needle members are hygienically maintained and deployed, and wherein a circumferential convex portion of the body member is on the radially inner side of the point end of the body member that extends in the axial direction of the forward end, a circumferential concave portion of the body member is on the part of the rear end complementary to the convex portion, and they fit into each other when axially adjacent puncture needles are connected, such that the puncture needles are connected in such a manner that removal of a puncture needle pulls the next puncture needle to the puncture position,
   the puncture needle cartridge comprising a plurality of puncture needle stopping members whose front ends are folded towards the inner wall of the puncture needle cartridge, wherein the stopping members engage a dent in a surface of each puncture needle body member and are located in the puncture needle cartridge at intervals of about the length of the body member of the puncture needle.

2. A puncture instrument as defined in claim 1 wherein said puncture needle cartridge holds each of the respective puncture needles in such a manner that the needle point end of the puncture needle is protected by the rear end of the body member of another puncture needle which is positioned immediately to the front of the puncture needle.

3. A puncture instrument as defined in claim 2 wherein the body member is an elastic deformation member,
   said puncture needle cartridge holds each puncture needle in a state where the needle point end of the puncture needle is protected by the rear end of the elastic deformation member of another puncture needle which is positioned immediately to the front of the puncture needle, and
   the rear end of the elastic deformation member of one puncture needle elastically grips the forward end of the elastic deformation member of the next puncture needle.

4. A puncture instrument as defined in claim 1 wherein said puncture needle cartridge is located in a cylindrical case, and comprises:
   a puncture needle cartridge stopping member for stopping the puncture needle cartridge in a predetermined position in an axis direction of the case,
   a biasing member for biasing the puncture needle cartridge in one direction in the case, and
   a puncture button for allowing the biasing member to move the puncture needle cartridge in the one direction, to start a puncture operation.

5. A puncture instrument as defined claim 1 further including
   a remaining quantity check means for checking the remaining quantity of the plurality of puncture needles in the puncture needle cartridge.

6. A puncture instrument as defined in claim 5 wherein said remaining quantity check means has, on a side surface of the puncture instrument, a puncture needle remaining quantity check window through which the puncture needles existing in the puncture needle cartridge can be visually checked.

7. A puncture instrument as defined in claim 1 wherein said puncture needle cartridge is detachably located in the puncture instrument.

8. A puncture needle cartridge comprising a plurality of puncture needles for puncturing the surface of a biologic body, wherein the cartridge is housed in a puncture instrument for performing seriatim puncturing with each of the puncture needles, wherein
   said puncture needle cartridge holds the plurality of puncture needles connected in series in an axis direction of the puncture instrument,
   each puncture needle comprises a body member and a needle member, wherein a base end of the needle member is secured in and substantially coaxial with the body member, and a needle point end protrudes forwardly; and the body member comprises a forward end and a rear end, wherein the forward end extends in the axial direction of the needle member to surround the needle point end, such that when connected to a second puncture needle, the forward end covers the outer surface of the rear end of the second puncture needle, and wherein the forward end and the rear end have substantially complementary shapes such that the needle members are hygienically maintained and deployed, and wherein a circumferential convex portion of the body member is on the radially inner side of the point end of the body member that extends in the axial direction of the forward end, a circumferential concave portion of the body member is on the part of the rear end complementary to the convex portion, and they fit into each other when axially adjacent puncture needles are connected, such that the puncture needles are connected in such a manner that removal of a puncture needle pulls the next puncture needle to the puncture position,
   the puncture needle cartridge comprising a plurality of puncture needle stopping members whose front ends are folded towards the inner wall of the puncture needle cartridge, wherein the stopping members engage a dent in a surface of each puncture needle body member and are located in the puncture needle cartridge at intervals of about the length of the body member of the puncture needle.

9. A puncture needle cartridge as defined in claim 8 wherein
   the forward end of the body member of each of the plurality of puncture needles is fitted to the rear end of the body member of another puncture needle which is positioned immediately to the front of the puncture needle.

10. A puncture needle cartridge as defined in claim 9 wherein
the body member is an elastic deformation member,
the rear end of the elastic deformation member of each puncture needle elastically grips the forward end of the elastic deformation member of the next puncture needle.

11. A puncture needle cartridge as defined in claim 9, wherein a fitting strength between the respective puncture needles is larger than a load capable of disengaging the puncture needle from a respective puncture needle stopping member.

12. A puncture needle cartridge as defined in claim 8 further including
a puncture needle retaining elastic member for holding a puncture needle positioned at the head of the puncture needle cartridge to prevent escape and dropout of the puncture needle from the puncture instrument body.

13. A puncture needle cartridge as defined in claim 12 wherein
said puncture needle retaining elastic member is integrated with the puncture cartridge.

14. A puncture needle cartridge as defined in claim 8 wherein
each of said puncture needles has, at its surface, two dents which are respectively engageable with a puncture needle stopping member for holding the puncture needle in the puncture needle cartridge and engaged with a puncture needle stopping elastic member for preventing escape and dropout of the puncture needle from the puncture needle cartridge.

15. A puncture needle cartridge as defined in claim 8 wherein
a puncture needle group comprising said plurality of puncture needles comprises a puncture needle cap which protects the needle point end of the puncture needle that is positioned to the front of the group.

16. A puncture needle cartridge as defined in claim 8 further including
a rotation stopping member for engaging the body of the puncture instrument to prevent the puncture instrument from rotating around the axis of the puncture instrument.

17. A puncture needle cartridge as defined in claim 8 further including a remaining quantity check means for checking the remaining quantity of the plurality of puncture needles in the puncture needle cartridge.

18. A puncture needle cartridge as defined in claim 17 wherein said remaining quantity check means comprises a variation of the respective colors of the plurality of puncture needles.

19. A puncture needle cartridge as defined in claim 17 wherein said remaining quantity check means comprises numbers (production codes) assigned to the respective puncture needles.

20. A puncture needle cartridge as defined in claim 8 of the present invention wherein
a puncture needle group comprising said plurality of puncture needles being connected in series is loaded in the puncture needle cartridge, by inserting new puncture needles in the puncture needle cartridge.

21. A puncture needle cartridge as defined in claim 20 wherein
said puncture needle group is loaded in the puncture needle cartridge in only one direction of the puncture needle cartridge.

22. A puncture needle cartridge as defined in claim 20 further including
an improper loading prevention return member for preventing the puncture needle group from being loaded in a wrong direction in the puncture needle cartridge.

23. A puncture needle cartridge as defined in claim 8 being detachable and attachable from/to the puncture instrument.

24. A puncture instrument set comprising
a puncture instrument having a puncture needle cartridge holding a plurality of puncture needles for puncturing the surface of a biologic body, said puncture instrument performing seriatim puncturing with each of the puncture needles, said puncture needles being connected in series in an axis direction of the cartridge, each puncture needle comprising a body member and a needle member, wherein a base end of the needle member is secured in and substantially coaxial with the body member, and a needle point end protrudes forwardly, the body member comprising a forward end and a rear end, wherein the forward end extends in the axial direction of the needle member to surround the needle point end, such that when connected to a second puncture needle, the forward end covers the outer surface of the rear end of the second puncture needle, and wherein the forward end and the rear end have substantially complementary shapes such that the needle members are hygienically maintained and deployed, and wherein a circumferential convex portion of the body member is on the radially inner side of the point end of the body member that extends in the axial direction of the forward end, a circumferential concave portion of the body member is on the part of the rear end complementary to the convex portion, and they fit into each other when axially adjacent puncture needles are connected, such that the puncture needles are connected in such a manner that removal of a puncture needle pulls the next puncture needle to the puncture position; and
a puncture needle replacement jig for setting the puncture needle cartridge at a puncture operation start position for a next puncture operation, and for removing a used puncture needle from the puncture needle cartridge, after puncturing by the puncture needle,
the puncture needle cartridge comprising a plurality of puncture needle stopping members whose front ends are folded towards the inner wall of the puncture needle cartridge, wherein the stopping members engage a dent in a surface of each puncture needle body member and are located in the puncture needle cartridge at intervals of about the length of the body member of the puncture needle.

25. A puncture instrument set as defined in claim 24 wherein
said puncture needle replacement jig includes a replacement jig return member which holds the puncture needle after puncturing, and removes the puncture needle from the puncture needle cartridge.

26. A puncture instrument set as defined in claim 24 wherein
said puncture needle replacement jig is for setting the puncture needle cartridge at the puncture operation start position simultaneously with removal of the puncture needle after puncturing.

27. A puncture instrument set as defined in claim 24 wherein
when the puncture needle is removed from the puncture needle cartridge by the puncture needle replacement jig after puncturing, each of the plurality of puncture needles connected in series in the puncture needle cartridge is moveable toward a front end of the puncture needle cartridge until it is held by a puncture needle stopping member which is capable of holding each puncture needle at a predetermined position in the puncture needle cartridge.

28. A puncture instrument set as defined in claim 24 further including
a puncture needle retaining elastic member for holding a puncture needle positioned at the head of the puncture needle cartridge to prevent escape and dropout of the puncture needle from the puncture instrument body;
wherein said puncture needle retaining elastic member is able to bend within an elasticity range of the puncture needle retaining elastic member due to fitting of the elastic member to a front end portion of the puncture needle replacement jig, thereby detaching the puncture needle positioned at the head of the puncture needle cartridge from the puncture needle retaining elastic member.

29. A puncture instrument set as defined in claim 24 wherein
said puncture instrument is provided with a remaining quantity check means for checking the remaining quantity of the plurality of puncture needles in the puncture needle cartridge.

30. A puncture instrument as defined claim 1, wherein
the forward end of the body member is a generally bell-shaped or cylindrical body of revolution open at the lowered end, and includes a radially inwardly protruding fully annular lip; and
the rear end of said body member includes an axially-extending hole for accommodating a needle point of another such puncture needle, and otherwise is a solid body of revolution whose exterior surface is substantially the geometric complement of the interior surface of the forward end, such that the forward end of the body member can fit over and grip the complementary rear end of another such puncture needle.

31. A puncture instrument as defined in claim 1, further comprising:
a cylindrical case, and
a loading cover on a side parallel to the axial direction of said cylindrical case, for permitting loading and unloading of the puncture needle cartridge into and out of the puncture instrument, wherein the puncture needle cartridge is removable.

32. A puncture instrument set comprising:
a puncture instrument having a puncture needle cartridge holding a plurality of puncture needles for puncturing the surface of a biologic body, said puncture instrument for performing seriatim puncturing with each of the puncture needles, said puncture needles being connected in series in an axial direction of the cartridge,
a puncture needle replacement jig for setting the puncture needle cartridge at a puncture operation start position for a next puncture operation, and for removing a used puncture needle from the puncture needle cartridge, after puncturing by the puncture needle,
each puncture needle including a first dent and a second dent in a surface thereof,
the puncture needle cartridge including a puncture needle retaining elastic member for engaging the first dent of the puncture needle body member which is positioned in a front end in the puncture needle cartridge to hold the puncture needle,
the puncture needle replacement jig including a replacement jig pressing part and a replacement jig return member, the replacement jig pressing part for pushing the puncture needle retaining elastic member outward to release engagement between the puncture needle retaining elastic member and the first dent in the puncture needle body member, and the replacement jig return member for engaging the second dent in the puncture needle body member to remove the puncture needle.

* * * * *